US010591403B2

(12) United States Patent
Roy et al.

(10) Patent No.: US 10,591,403 B2
(45) Date of Patent: Mar. 17, 2020

(54) MULTIPLEXED ANALYSIS OF CELL-MATERIALS IN NICHES

(71) Applicant: Georgia Tech Research Corporation, Atlanta, GA (US)

(72) Inventors: Krishnendu Roy, Atlanta, GA (US); Kirsten Parratt, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 16/085,077

(22) PCT Filed: Mar. 16, 2017

(86) PCT No.: PCT/US2017/022762
§ 371 (c)(1),
(2) Date: Sep. 14, 2018

(87) PCT Pub. No.: WO2017/161149
PCT Pub. Date: Sep. 21, 2017

(65) Prior Publication Data
US 2019/0078994 A1 Mar. 14, 2019

Related U.S. Application Data

(60) Provisional application No. 62/308,902, filed on Mar. 16, 2016.

(51) Int. Cl.
*G01N 21/85* (2006.01)
*G01N 15/14* (2006.01)
(Continued)

(52) U.S. Cl.
CPC ...... *G01N 15/147* (2013.01); *B01L 3/502761* (2013.01); *G01N 15/1434* (2013.01);
(Continued)

(58) Field of Classification Search
CPC ...... G01N 21/314; G01N 21/05; G01N 21/85; G01N 21/253; G01J 3/46
(Continued)

(56) References Cited

U.S. PATENT DOCUMENTS

2008/0241820 A1 10/2008 Krutzik et al.
2014/0224710 A1 8/2014 Di Carlo et al.

FOREIGN PATENT DOCUMENTS

WO 2014/117784 8/2014

OTHER PUBLICATIONS

International Search Report and Written Opinion from application No. PCT/US17/022762 dated May 25, 2017 (15 pages).

*Primary Examiner* — Md M Rahman
(74) *Attorney, Agent, or Firm* — Troutman Sanders LLP; Ryan A. Schneider

(57) ABSTRACT

Embodiments of the present disclosure can comprise a method for multiplexed analysis. The method can comprise acquiring interrogation data associated with a microstructure in a population and analyzing the microstructure based on the interrogation data. In some embodiments, the microstructure can have a different shape than at least another microstructure in the population and comprise a plurality of cells. Additionally, the acquiring the interrogation data can comprise acquiring interrogation data of microstructures in a population at a structure concentration of at least 100 microstructures/μL. Therefore, in some embodiments, acquiring the interrogation data can comprises flowing the population through a flow cytometer.

19 Claims, 26 Drawing Sheets

(51) Int. Cl.
*G01N 33/50* (2006.01)
*B01L 3/00* (2006.01)
*G01N 21/64* (2006.01)
*G01N 33/569* (2006.01)
*G01N 15/10* (2006.01)

(52) U.S. Cl.
CPC ..... *G01N 15/1475* (2013.01); *G01N 15/1484* (2013.01); *G01N 21/6486* (2013.01); *G01N 33/50* (2013.01); *G01N 33/569* (2013.01); *B01L 2200/0652* (2013.01); *G01N 2015/1006* (2013.01); *G01N 2015/149* (2013.01); *G01N 2015/1445* (2013.01)

(58) Field of Classification Search
USPC ........................................................ 356/410
See application file for complete search history.

MULTIPLEXED ANALYSIS OF CELL-MATERIALS IN NICHES

CROSS-REFERENCE TO RELATED APPLICATIONS

This application is a U.S. National Stage of International Patent Application No. PCT/US2015/032329, filed May 24, 2015, entitled "Chip-Scale Embedded Carbon Nanotube Electrochemical Double Layer Supercapacitor", which claims priority to U.S. Provisional Patent Application No. 62/002,812, filed May 24, 2014, entitled "Chip-Scale Embedded Carbon Nanotube Electrochemical Double Layer Supercapacitor," and U.S. Provisional Patent Application No. 62/156,977, filed May 5, 2015, entitled "Chip-Scale Embedded Carbon Nanotube Electrochemical Double Layer Supercapacitor," the contents of of which are all fully incorporated herein by reference.

GOVERNMENT SPONSORSHIP

This invention was made with government support under Grant No. CBET-1417134 awarded by the National Science Foundation. The government has certain rights in the invention.

TECHNICAL FIELD

Embodiments of the present disclosure relate generally to multiplexed analysis of microstructures, such as cell-material niches.

BACKGROUND

In cancer research, it is becoming increasingly critical to study tumor cells in the context of their microenvironment (e.g. in the presence of stromal and/or immune cells and within a relevant 3D niche). This is not only important for understanding fundamental tumor biology, but also to develop the next generation of anti-tumor therapeutics and interventions. The ability to study tumor cell interactions with other niche components (fibroblasts, MDSCs, macrophages and dendritic cells (DCs), regulatory and effector T cells, B cells, tumor-ECM, tumor vasculature etc.) in a quantitative manner, within highly-controlled synthetic microenvironments, could provide significant new information on the growth, proliferation, cell-cell and cell-matrix communication of various tumors while allowing study of how external manipulations (e.g. drugs, immunotherapies, radiation therapy etc.) affect tumors in a more native-like microenvironment.

In vitro 3D systems of synthetic or ECM-derived biomaterials containing cells or organoids have become essential for better understanding of cell biology, unraveling complex disease processes, and developing new biomedical materials to restore function in diseased tissues or deliver therapeutic cells. Biological assays inherently suffer from high "noise" that limits experimental reproducibility. Cells in particular are highly sensitive to manipulations and changes to their microenvironment. Thus, measurement-confidence in cell-behavior requires high replicate numbers to generate high statistical power, reduce false positives, and identify subtle changes. Unfortunately, existing methods are time-intensive, low-throughput, destructive, or limit further sample manipulation. However, such approaches suffer from a lack of high throughput analytical methods that allows rapid measurement of many cell parameters inside 3D niches in a non-destructive manner with high statistical confidence.

Flow cytometry allows for the collection of a large number of unique events in a short time period, which can be combined to build a picture, characteristic of a large population. Because multiple fluorescent channels can be used concurrently, flow cytometry enables the user to precisely define multiple values of interest and use these to gate for specific sections of interest. However, fluorescence alone gives very little multiplexing capability compared to hundreds of parameters that one can envision studying. Even the CyTOF method allows ~40-60 variables to be studied, but uses a destructive mass spec-based process.

It is with respect to these and other considerations that the various aspects of the disclosed technology as described below are presented.

SUMMARY

Aspects of the present disclosure relate to methods for multiplexed analysis of cell niches. An embodiment of the present disclosure can comprise a method for multiplexed analysis. The method can comprise acquiring interrogation data associated with a with a microstructure in a population at a structure concentration of at least 100 microstructures/µL and analyzing the microstructure based on the interrogation data, wherein the microstructure has a different shape than another microstructure in the population and comprises a plurality of cells.

In some embodiments, acquiring the interrogation data can comprise flowing the population through an imaging flow cytometer and in other embodiments, acquiring the interrogation data can comprise flowing the population through a non-imaging flow cytometer. Additionally, in some embodiments, the acquired interrogation data can be indicative of at last one of the shape, size, or fluorescence of the microstructure.

The microstructure in the population can be any structure having at least one dimension on the micro-scale. In some embodiments, the microstructure can comprise a plurality of cells suspended in a polymer. In some embodiments, the cell concentration of the cells within the microstructure can be between $10^6$ and $10^7$ cells/µL. In some embodiments the cell concentration of the cells within the microstructure can be $10^5$ cells/µL or less. In some embodiments, plurality of cells comprises at least one of stem cells, cancer cells, and stromal cells, or a combination thereof.

In some embodiments, the population of microstructures can comprise a plurality of microstructures. Therefore, the population of microstructures can comprise various subpopulations of microstructures characterized by having differing shapes, sizes, and fluorescence. For instance, in some embodiments, a microstructure in the population can have a different size than another microstructure in the population. In other embodiments, a microstructure in the population can have a different fluorescence than other microstructure in the population. In some embodiments, a microstructure in the population can comprise a different size and shape than another microstructure in the population, and in other embodiments, a microstructure in the population can comprise a different size, shape, and fluorescence than another microstructure in the population. In some embodiments, the population of microstructures can comprise at least 3500 microstructures. In other embodiments, the population of microstructures can comprise at least 49,500 microstructures.

In some embodiments, analyzing the micro-structure based on the interrogation data comprises identifying at least one of the shape, size, and fluorescence of the microstructure. Additionally, in some embodiments, analyzing the microstructure can further comprise indexing the microstructure based on a pre-determined barcoding system using the identified at least one of shape, size, and fluorescence of the microstructure. In some embodiments, the pre-determined barcoding system can comprise at least 300 distinct barcodes corresponding to size, shape, and fluorescence, or a combination thereof.

Another embodiment of the present disclosure can include a method comprising: acquiring interrogation data associated with a micro-structure in a population at a structure concentration of at least 100 microstructures/μL; identifying at least one of the shape, size, and fluorescence of the microstructure from the interrogation data; and indexing the microstructure based on a pre-determined barcoding system; wherein the microstructure has a different shape than another microstructure in the population and comprises a plurality of cells.

Another embodiment of the present disclosure can comprise a method for multiplexed analysis. The method can comprise acquiring interrogation data associated with a population at a structure concentration of at least 100 microstructures/μL, the population comprising a plurality of micro-structures; identifying at least one of the shape, size, and fluorescence of the plurality of micro-structures from the interrogation data; and sorting the population based on at least one of size, shape, and fluorescence of the plurality of microstructures; wherein at least one microstructure has a different shape than at least another microstructure in the population and comprises a plurality of cells.

An embodiment of the present disclosure can include a method for multiplexed analysis. The method can comprise: acquiring interrogation data using a flow cytometer, the interrogation data associated with a population comprising a plurality of micro-structures; identifying at least one of the shape, size, and fluorescence of the plurality of microstructures based on the interrogation data; and analyzing the population based on at least one of shape, size, and fluorescence of the plurality of microstructures; wherein at least one microstructure in the population has a different shape than at least another microstructure and comprises a plurality of cells. In some embodiments, the flow cytometer can be an imaging flow cytometer and the interrogation data can comprise image data.

An embodiment of the present disclosure can include a method for high-throughput analysis of cellular niches. The method can comprise flowing a population of microstructures through a tube of a flow cytometer, the population of cell-material composites having individual cell-material composites of various shapes; interrogating each microstructure of the population of microstructures, as the microstructure passes an interrogation point; acquiring individualized data associated with each microstructure, the individualized data comprising information corresponding to the shape of the microstructures; and sorting the population of microstructures based on shape.

Other aspects and features according to the example embodiments of the disclosed technology will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

DETAILED DESCRIPTION

Figure 1:
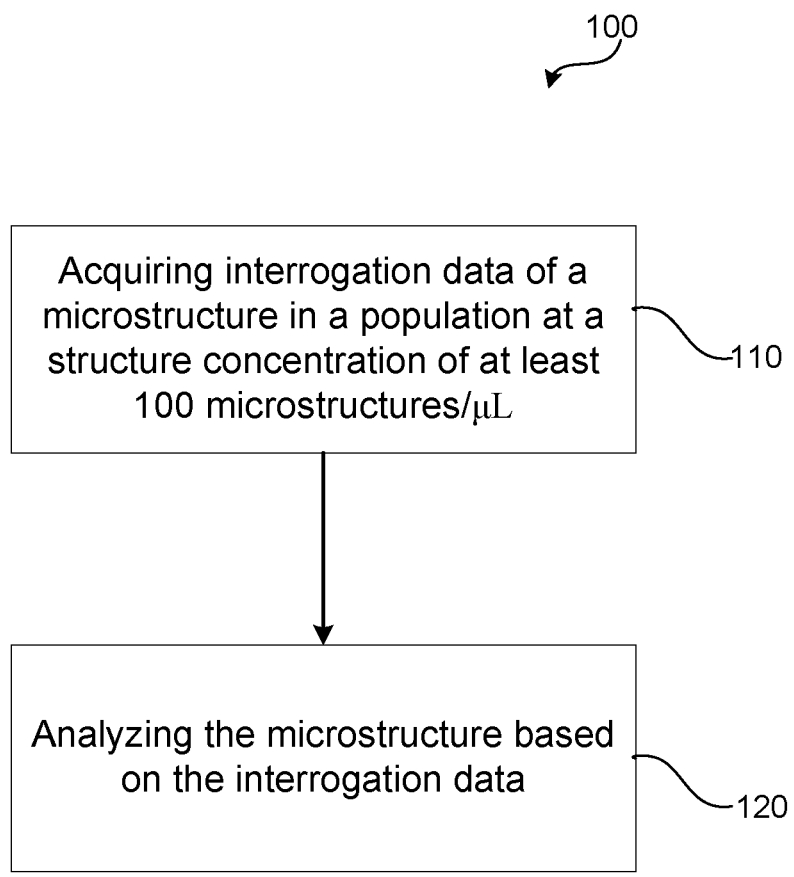
FIG. 1 is a flow diagram of a method for multiplexed analysis, according to an embodiment of the present disclosure.

In some aspects, the present disclosure relates multiplexed analysis of microstructures, such as cell-material niches. Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

A detailed description of aspects of the present disclosure, in accordance with various example embodiments, will now be provided with reference to the accompanying drawings. The drawings form a part hereof and show, by way of illustration, specific embodiments and examples. In referring to the drawings, like numerals represent like elements throughout the several figures.

Embodiments of the presently disclosed system and methods for multiplexed analysis of microstructures can enable very high-replicate, high throughput, rapid, and non-destructive analyses of various structures including 3D cell-material niches or organoids. Embodiments of the present disclosure can achieve very high "n" by using hundreds and thousands of microstructures, fabricated using simple lithographic techniques. Specifically, in some embodiments, microstructures can be created to mimic specific cellular microenvironments. Aspects of cell microenvironments can be mimicked by altering the shape and size of the microstructures. Additionally, in some embodiments, shape and size, combined with fluorescence tagging can be used to uniquely barcode the material composition of each type of microstructure. Including shape, in addition to size and fluorescence, allows for a unique barcode having increased multiplexing capability, many folds beyond known analytical approaches. To achieve high throughput, rapid, and high replicate analysis of microstructures, a high throughput analytical system, such as flow cytometry, can be used to analyze a population of microstructures and achieve multiparametric data analysis.

Despite the tremendous impact that flow cytometry can have on biological assays, the technique has been primarily restricted to single-cell analyses (within a population) and its application to biomaterials has not yet been realized. Embodiments of the present disclosure can adapt high-throughput analytical systems, like flow cytometry, to analyze 3D microstructures. Known flow cytometry methods are designed to record data on hundreds of individual events per second in tens of fluorescence channels. Flow cytometers can enable direct imaging of each event, thus allowing shape to be a distinguishing parameter in analysis, in addition to size and fluorescence.

FIG. 1 is a flow diagram of an exemplary but non-limiting method 100 for multiplexed analysis, according to an embodiment of the present disclosure. As used herein, multiplexed can refer to methods or assays permitting simultaneous or near-simultaneous measurement of multiple analytes in a single experimental cycle. In some embodiments, the method 100 can comprise acquiring interrogation data associated with a microstructure in a population (110) and analyzing the microstructure based on the interrogation data (120). Embodiments of the present disclosure can be advantageous as they can permit acquisition of interrogation data from and analysis of microstructures within a population having different shapes, as discussed in greater detail with respect to FIGS. 6-18*b*. As discussed previously, including shape as a feature for analysis can increase the multiplexing capabilities of analysis of microstructures in a population. Therefore, in an exemplary but non-limiting embodiment, the microstructure in the population can have a different shape than at least another microstructure in the population.

Figure 2:
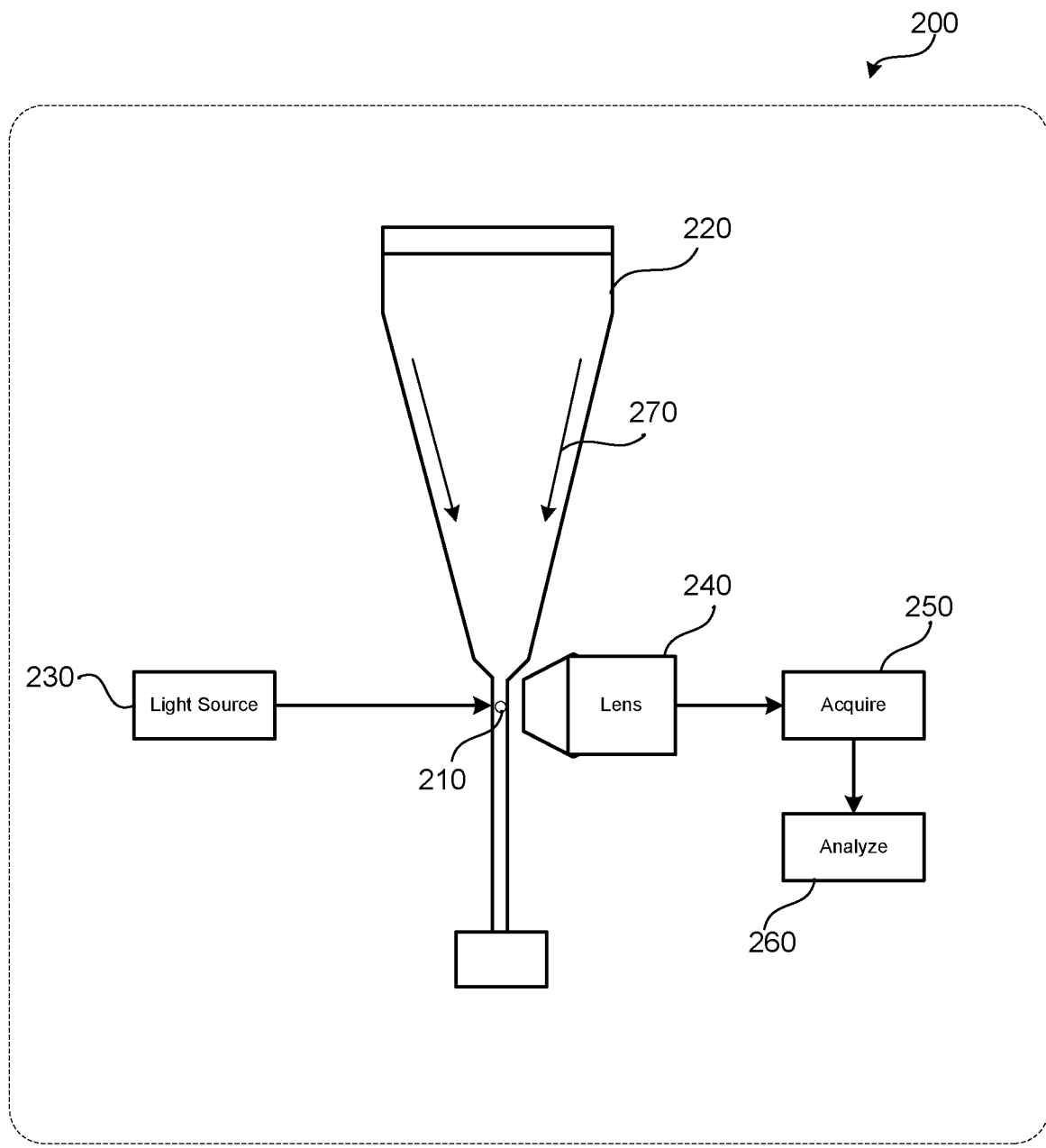
FIG. 2 is a schematic of an example high throughput analytical system, functionally descriptive of a flow cytometer, according to an embodiment of the present disclosure.

In some embodiments, acquiring interrogation data can comprise flowing the population of microstructures through a high throughput analytical system. In some embodiments, the high throughput analytical system can use flow cytometry for analyzing a population of microstructures. A schematic diagram of an exemplary high throughput analytical system 200, functionally descriptive of a flow cytometry platform, is illustrated in FIG. 2. The high throughput analytical system 200 can acquire interrogation data associated with an object 210 entrained in a fluid flow cell 220. The object 210 can be, for instance, a microstructure entrained in a fluid flow cell 220.

Moving objects 210 in the fluid flow cell 220 can be illuminated using a light source 230 as the moving objects pass an interrogation point (230, 240, 250). The light source 230 may be any light source now known or subsequently developed and can include a laser, a light emitting diode, a filament lamp, a gas discharge arc lamp, or other suitable light emitting source. Additionally, aspects of the high throughput analytical system 200 may include other optical conditioning elements such as lenses (e.g. objective lens 240), apertures, and filters for delivering broadband or one or more desired wavelengths or wavebands of light to the object 210 with an intensity required for detection of the velocity and one or more other characteristics of the object (such as interrogation data comprising the size, shape, and/or fluorescence of the object). Light from the object 210 can be directed to a data analytical unit for acquisition 250 and analysis 260 of interrogation data of the object 210, as described above with respect to FIG. 1.

Figure 9:
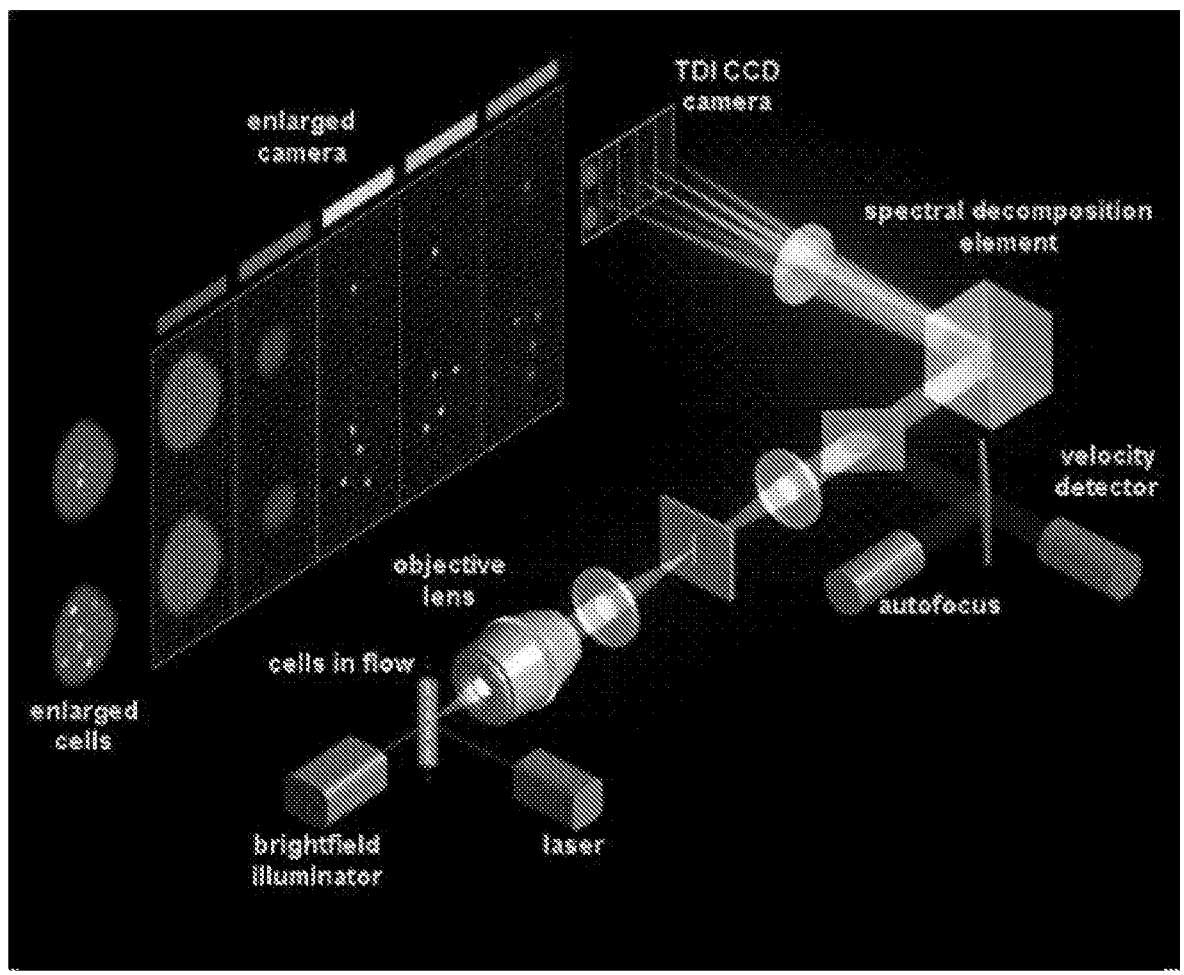
FIG. 9 is a schematic of another example of a high throughput analytical system functionally descriptive of an imaging flow cytometer, according to an embodiment of the present disclosure.

In some embodiments, the high throughput analytical system 200 can be an imaging flow cytometer. Imaging flow cytometers, unlike other flow cytometers, can acquire images of interrogated objects 210. So, for instance, imaging flow cytometers can include a camera capable of taking microscopic images of objects 210 and acquire both qualitative and quantitative data of objects in a sample. FIG. 9 (discussed in greater detail below) illustrates an exemplary setup of an imaging flow cytometer as available in the ImageStream MarkII User's Manual. In other embodiments, the high throughput analytical system can be a flow cytometer. Other non-imaging flow cytometers can permit for acquisition of scattered light data of the object, physical counting of objects, or physical sorting of object based on size or shape, such as a fluorescence-activated cell sorting (FACS).

As stated above, the object 210 can be entrained in a fluid flow cell 220. As such, the object 210 (such as a microstructure) can be suspended in a solution to permit flowing the object through the fluid flow cell 220 during interrogation. Additionally, as the object is flowed through the fluid flow cell 220, a sheath fluid 270 can be added to promote laminar flow of objects 210 in the fluid flow cell 220.

The mixture flowed through the fluid flow cell 220 can comprise, for instance, a plurality of microstructures suspended in a solution. High replicate numbers can be achieved by creating at least $10^4$ microstructures per 2 μL of precursor solution using the methods as described, for example, at FIG. 3. The described methods can be advantageous as they can permit high replicate analysis of microstructures using the high throughput analytical system (e.g. flow cytometry or imaging flow cytometry). The replicate number in high throughput analytical systems can be important because it can permit high statistical significance, reduce false positives, and identify subtle changes in a population. Those skilled in the art will understand that replicate number can be increased or decreased as desired. For instance, in some embodiments, the at least $10^6$ microstructures can be fabricated per 2 μL of precursor solution. Additionally, in some embodiments, from about $10^4$ to about $10^6$ microstructures can be fabricated per 2 μL of precursor solution.

While discussed in terms of flow cytometry and imaging flow cytometry, those skilled in the art will understand that the high throughput analytical system can be any high throughput analytical system known or later developed. In some embodiments, high throughput can refer to the ability to collect at least 50 events/μL, 100 events/μL, at least 200 events/μL, at least 300 events/μL, and at least 500 events/μL. The flow rate used to flow microstructures through the high throughput analytical system can be any standard flow rate or range of flow rates as understood by those skilled in the art of, for instance, any non-imaging flow cytometer or imaging flow cytometer now known or later developed. For instance, in some embodiments, non-imaging flow cytometers or imaging flow cytometers can achieve at least about 250 events/s, at least about 500 events/s, at least about 1000 events/s, at least about 5,000 events/s, and at least about 10,000 events/s. As used herein, event can refer to detection of at least one microstructure as the microstructure is subjected to high throughput analysis.

As illustrated with respect to FIG. 1, methods for multiplexed analysis can comprise acquiring interrogation data (110). Interrogation data can include, for instance, data acquired by a high throughput analytical system at an interrogation point. In some embodiments, the interrogation data can be indicative of at least one of the shape, size, or fluorescence of a microstructure as the microstructure passes the interrogation point. In an embodiment using an imaging flow cytometer, the interrogation data can be a plurality of images acquired of the microstructures in the population. Therefore, in some embodiments, acquiring individualized data associated with each microstructure can comprise acquiring image data. In embodiments utilizing an imaging flow cytometer, the images obtained of each microstructure can be color images and permit identification of fluorescent tagging. In other embodiments, the flow cytometer can be a conventional flow cytometer that acquires data associated with scattered light.

Imaging flow cytometers can permit acquiring images of individual subjects in a population as the subject passes the interrogation point. As described herein, an image of respective microstructures in the population can be obtained as a microstructure passes an interrogation point. Those skilled in the art will appreciate, however, that in some instances more than one microstructure may pass an interrogation point at a single time. Therefore, acquired image data may include information corresponding to more than one microstructure.

As used herein, microstructure can include any structure with at least one dimension on the micro-scale. At least a portion of the microstructures within a population can include a plurality of cells trapped within a material. For instance, the plurality of cells can include biological cells but could also include particles, molecules, or beads, or a combination thereof. In the context of biological cells, the cells may be living or dead. In some embodiments, the plurality of microstructures can comprise a plurality of cells suspended in a polymer. The plurality of cells may be contained within the polymer or present on a surface of the microstructure or a combination thereof. In an example embodiment, the microstructures can comprise a plurality of microgels (used interchangeably with micro-hydrogels or hydrogels) with a plurality of cells trapped within the microgel (as described in greater detail with respect to FIG. 3). In other embodiments, the microgels can comprise analyte-sensing microparticles.

The plurality of cells within the microstructure can be biological cells. In some embodiments the plurality of cells can comprise at least one of a cancer cells, stem cells, dendritic cells, effector T cells, regulator T cells, and B cells. Before analysis of the microstructures, the plurality of cells can, in some instances, be subjected to external stimuli such as cytotoxic drugs and cytokines. Then, individual cells within the microstructure can be tagged with one or more fluorescence tags indicative of the external stimuli or some other cellular property of interest. Additionally, the cells can be cells in culture derived from an animal cell line and cultured or the cells can be cells obtained from a patient, such as lymph-node-biopsy-isolated tumor/stromal immune cells. Additionally, the cells within the microstructure can comprise a variety of different cell types for creating, for example, a microenvironment. As an example, the microstructures can comprise tumor and stromal cells along with primary macrophages. For instance, a single microstructure may comprise CD11b+Gr-1/Ly-6G+ MDSCs, CD4+Foxp3+ Treg cells, CD4+ and CD8+ T cells, CD11c+ DCs and CD11b+F4/80+ macrophages (all from spleen), and dermal skin fibroblasts.

Figure 3:
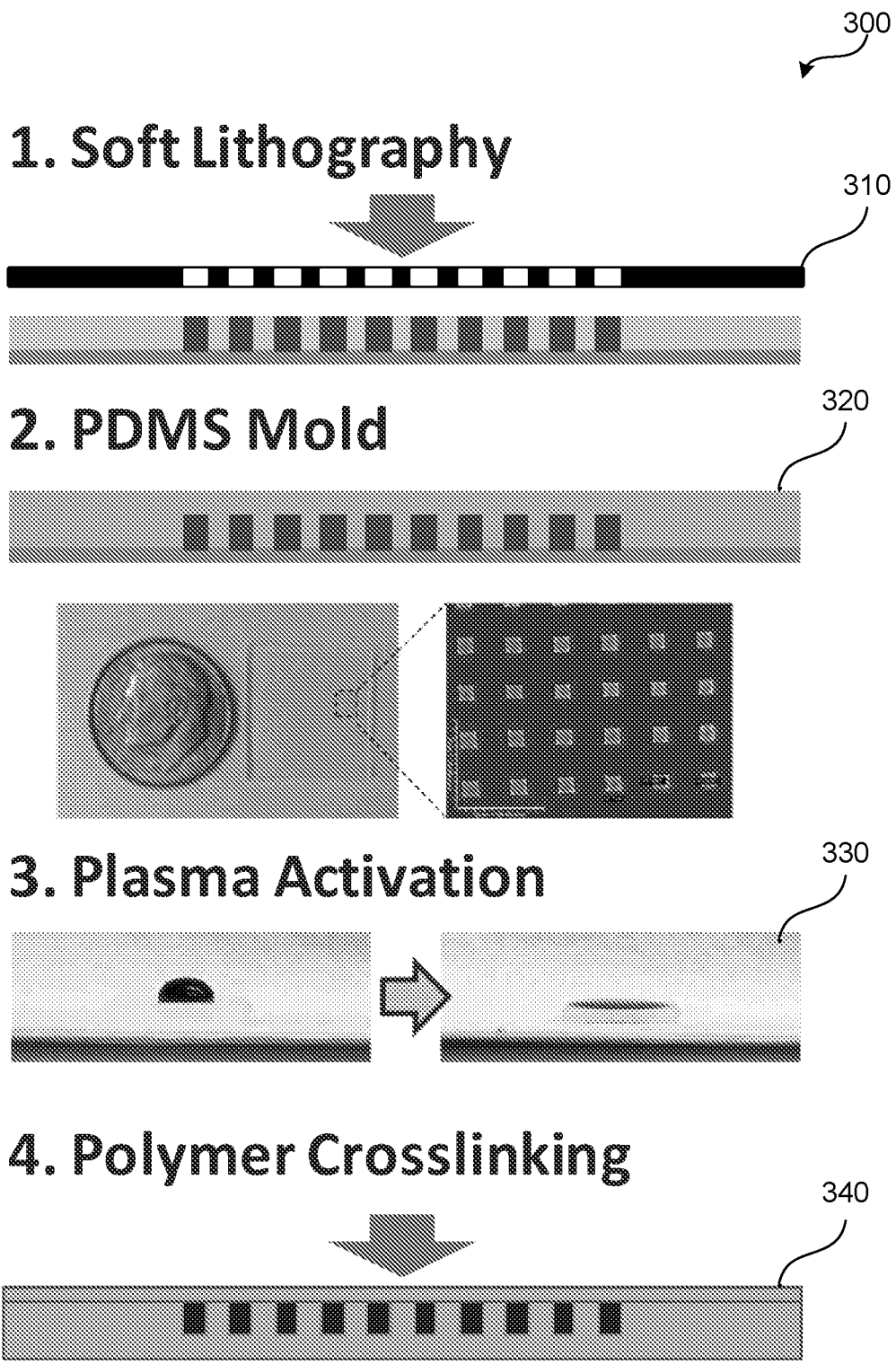
FIG. 3 is a schematic of a method for fabricating microstructures for use in a method for multiplexed analysis, according to an embodiment of the present disclosure.

FIG. 3 illustrates an exemplary method 300 for fabrication of microstructures. In some embodiments, the microstructures can be fabricated using lithographic techniques. A prepolymer suspension can be created by combining cells in media with a prepolymer. Photolithography 310 can then be used to fabricate a mold 320 comprising a plurality of patterns in a silicon wafer. In embodiments incorporating a hydrophobic mold, the mold can be plasma-activated 330 to render the mold hydrophilic to accept the prepolymer suspension. The prepolymer suspension can then be forced into the patterns and polymerized 340 within the mold, to form a plurality of microstructures.

Each microstructure can therefore comprise varying concentrations of cells. For instance, in some embodiments, the microstructures can comprise a high concentration of cells. For instance, the microstructures can comprise between about $10^6$ cells/mL to about $10^7$ cells/mL. Higher cell concentrations can permit mimicking of organoids or tissue microenvironments. In other embodiments, the microstructures can comprise a lower concentration of cells. For instance, the microstructures may comprise about $10^5$ cells/mL or fewer. Lower cell concentrations within microstructures can mimic biomaterial-cell interactions within, for instance, a cell niche. Cell concentrations within a microstructure can be ascertained with respect to the cell count within a microstructure having a known size. As such, according to embodiments of the present disclosure, the concentration of cells in the microstructures can be varied as desired in order to test properties of cells within varying micro-environments.

The population of microstructures can comprise individual microstructures having differing or varying two-dimensional shapes. As used herein, shape can refer to the two-dimensional shape of a microstructure. Additionally, in some embodiments, the shape of the cell-material composite may vary through the volume of the cell-material composite.

The described methods for multiplexed analysis can be applied to diverse populations of microstructures, including cell populations of differing size, shape, and color to increase multiplexing. In some embodiments, the population of microstructures can comprise various subpopulations of shapes, each subpopulation having differently shaped microstructures. The microstructures can be any shape including, circles, triangles, ellipse, oval, square, rectangle, right triangle, equilateral triangle, or other polygons.

In some embodiments, other properties of the microstructures can vary within the population of microstructures. For instance, in some embodiments the population of microstructures can comprise subpopulations of microstructures having different sizes. As used herein, size can refer to any measurement associated with the dimensions of the microstructures, including height, length, area, thickness, volume, diameter etc. For instance, the microstructures can have different areas, for instance at least about 20, at least about 100, at least about 200, at least about 400, at least about 600, and at least about 3600 $\mu m^2$. In some embodiments, the area of the microstructures can be between at about 20-3600 $\mu m^2$, about 100-3600 $\mu m^2$, about 200-3600 $\mu m^2$, about 400-3600 $\mu m^2$, about 600-3600 $\mu m^2$, about 200-400 $\mu m^2$, about 600-1000 $\mu m^2$, and about 1000-3000 $\mu m^2$. Those skilled in the art would understand that the area of the microstructures can be increased or decreased as desired. In some embodiments, the microstructures can have various lengths, including at least about 20, at least about 40, and at least about 60 $\mu m$ lengths. As used herein, length can refer to the distance across a microstructure, the diameter, or the height of the microstructure. The length need not, for instance, be the longest portion of the microstructure and may instead describe portions of the microstructure that are smaller than the longest portion of the microstructure.

In embodiments including flow cytometry, like that illustrated at FIG. 2, the area or length of the microstructures can be increased or decreased as desired, so long as the microstructures can fit through the narrowest portion of the fluid flow cell of the flow cytometer. In an exemplary but non-limiting embodiment, the size of the microstructures can be less than about half the diameter of the fluid flow cell of the flow cytometer. In another embodiment, the size of the microstructures can be less than about a third of the diameter of the fluid flow cell of the flow cytometer. As will be appreciated by those skilled in the art, the size of the microstructures can be optimized so as to prevent clogging while increasing the multiplexing capabilities of the assay.

In some embodiments, the microstructures can comprise a plurality of size subpopulations for each shaped microstructures. In an example embodiment, the population of microstructures can comprise square, circle, equilateral triangle, and right triangle subpopulations, and further comprise subpopulations of each shape having at least about 20, at least about 40, and at least about 60 $\mu m$ lengths resulting in 12 separate subpopulations.

In some embodiments, some or all of the microstructures can be tagged with fluorescent markers. For instance, microstructures themselves can be tagged with a variety of fluorescent markers. In some embodiments, the cells within the microstructures can be tagged with a variety of fluorescent markers to allow for increased multiplexing capabilities. Therefore, a single microstructure could, for instance, be tagged with multiple fluorescent markers indicative of a variety of cellular properties. Microstructures can be tagged with any fluorescent markers now known or later developed that can be detected using a high throughput analytical system, including fluorescent nano/microparticles, antibodies, fluorophores, or other fluorescent dyes. Interrogation data corresponding to fluorescence can be, for instance, fluorescent intensity of the fluorescence marker.

In an exemplary, but non-limiting embodiment, the sample for analysis can comprise a population of microstructures. One advantage of the presently disclosed systems and methods is the ability to analyze microstructures in a population with high-replicate numbers to improve statistical strength of an experiment. Therefore, such high replicate numbers can permit analysis of populations of microstructures on the order of at least about 1,000, at least about 3,500, at least about 5,000, at least about 10,000, or at least about 50,000 microstructures, depending on the desired experimental set-up. In some instances, the replicate number may correspond to the number of microstructures within a subpopulation of microstructures having a similar shape or size. For instance, such replicate numbers can include at least about 40,000, at least about 50,000, at least about 90,000, at least about 250,000, at least about 1,000,000, at least about 3,000,000, and at least about 8,000,000 replicates.

The population of microstructures can include various subpopulations. For instance, the subpopulations of microstructures can include different shapes, sizes, and fluorescence of the microstructures within the subpopulation. For example, the population of microstructures can include a subpopulation of circular microstructures and a subpopulation of square microstructures. In an embodiment, the population of microstructures can include a plurality of subpopulations having microstructures of a different size. In an embodiment the population of microstructures may have a plurality of subpopulations having microstructures having a different fluorescence. As discussed previously, embodiments of the present invention can include fluorescence-tagged microstructures, or the plurality of the cells within the microstructure can be tagged. For instance, in an embodiment, a single microstructure could be fluorescence-tagged for a variety of properties and therefore emit various colors or fluorescent intensities.

Figure 4:
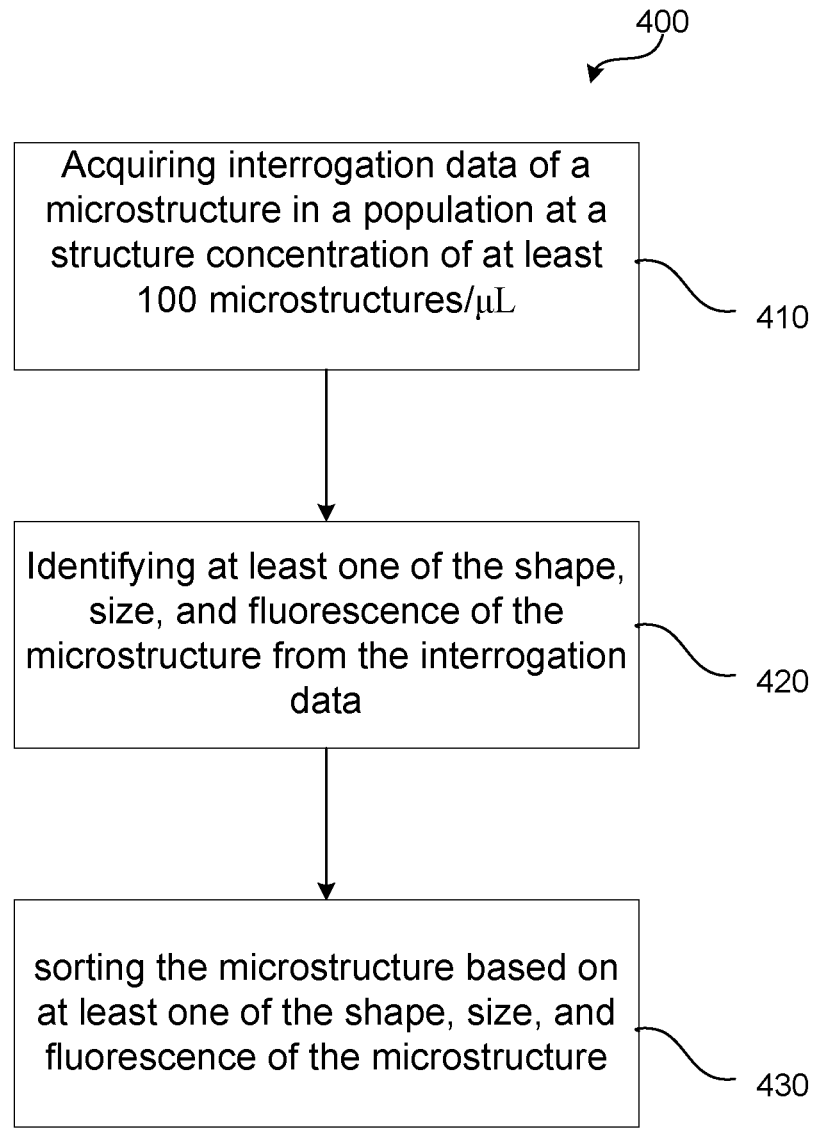
FIG. 4 is another flow diagram of a method for multiplexed analysis, according to an embodiment of the present disclosure.

Following the acquiring step 110, as illustrated in FIG. 1, the microstructure can be analyzed based on the interrogation data (120). FIG. 4 illustrates another exemplary method 400 including additional steps for analyzing microstructures or the population of microstructures. In some embodiments, as illustrated at FIG. 4, analyzing the microstructures can comprise identifying at least one of the shape, size, and fluorescence of the microstructure from the interrogation data (420) and sorting the microstructure based on at least one of the shape, size, and fluorescence of the microstructure (430). In some embodiments, the population of microstructures can comprise a plurality of microstructures and the analyzing step (120) can be performed on at least a portion of the microstructures in the population.

In some embodiments, the step of sorting (430), as described with reference to FIG. 4, can be achieved based on at least one of size, shape, and fluorescence of the microstructures. For instance, the microstructures can be sorted just based on shape. In some embodiments, the microstructures can be sorted by shape and fluorescence or size and shape. In other embodiments, the microstructures can be sorted based on size and shape or by size, shape, and fluorescence.

In some embodiments, sorting the population of microstructures (430) based on shape can comprise identifying a plurality of features corresponding to the shape of the microstructures and gating the population of microstructures based on at least one of size, shape, and fluorescence. In some embodiments, gating can comprise separation of microstructures in a population based on a plurality of defined gating parameters. In some embodiments, the number of gating parameters can be at least 2, at least 4, at least 8, at least 12, and at least 14 gates depending on the size, shape, and fluorescence of the microstructures in the population.

In some embodiments, analysis of the microstructures within the population can be facilitated by applications now known or later discovered as discussed in greater detail below. In some embodiments, identifying the plurality of features corresponding to the shape of the microstructures (420), as discussed with respect to FIG. 4, can include identifying at least one of aspect ratio, lobecount, symmetry, and circularity. Gating can then comprise plotting the plurality of microstructures based on one or more of the identified features. For instance, in an example embodiment, the microstructures can be gated based on symmetry to facilitate sorting based on size and shape. In another embodiment, the plurality of microstructures can be gated based on symmetry and circularity.

One benefit of the presently disclosed method for high-throughput analysis of cell niches is the ability to accurately sort microstructures based on at least one of size and shape. In some embodiments, the microstructures can be sorted with at least about 80% accuracy. In other embodiments, the microstructures can be gated based on at least one of size and shape with at least about 90% accuracy. In some embodiments, the microstructures can be sorted with at least about 40% accuracy, with at least about 50% accuracy, and with at least about 70% accuracy. In some embodiments, the microstructures can be sorted with between about 40% and about 50% accuracy, between about 50% and about 70% accuracy, between about 70% and about 80% accuracy, between about 80% and about 90% accuracy, and greater than about 90% accuracy.

In some embodiments, the step of analyzing (120) can be achieved with the assistance of a processor capable of executing a plurality of instructions stored in a memory. In some embodiments, the step of analyzing can be achieved physically, such as with FACS which can permit physical sorting, counting, and other analysis without the assistance of a processor.

Another important aspect of the present disclosure is the ability to create barcodes of cell-material populations to provide for increased multiplexing. In some embodiments, the barcoding system can comprise at least 300 different barcodes corresponding to differing shapes, sizes, and fluorescence of the microstructures. In some embodiments the barcode system can have at least 500 different barcodes corresponding to differing shapes, sizes, and fluorescence of the microstructures. In other embodiments, the barcode system can have around 1600 different barcodes.

Figure 5:
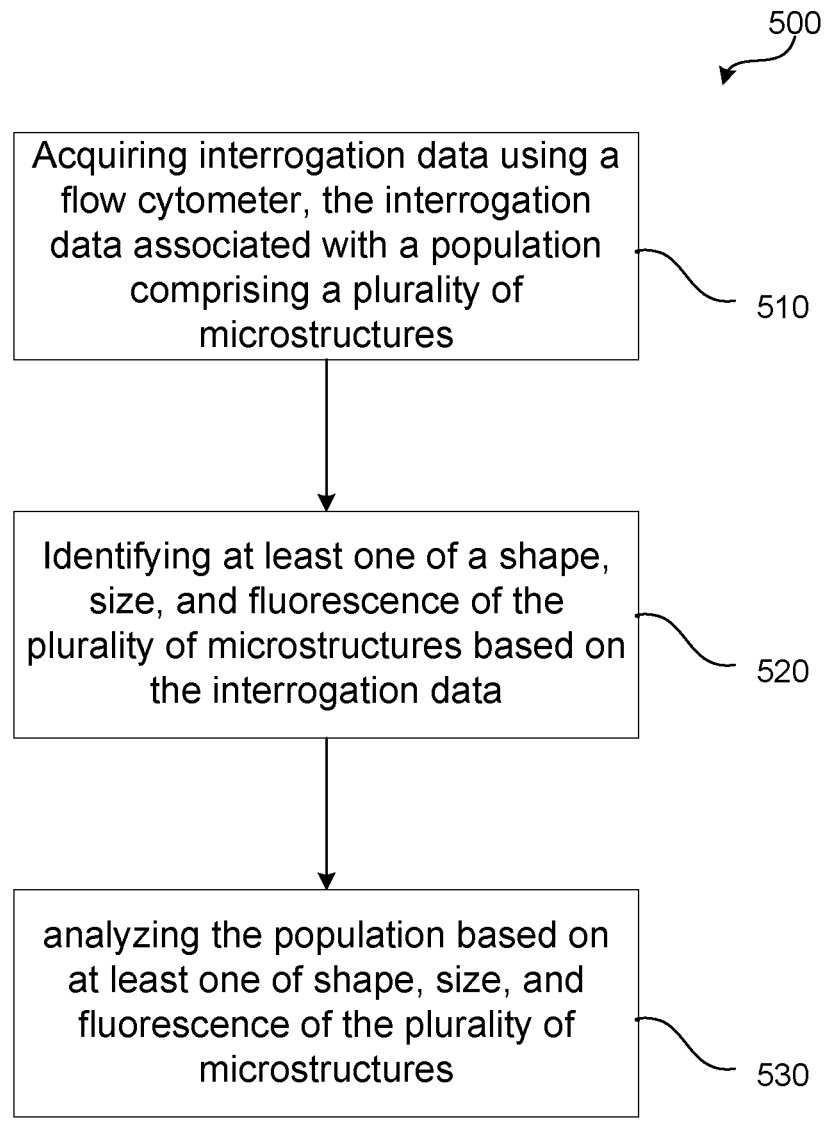
FIG. 5 is another flow diagram of a method for multiplexed analysis, according to an embodiment of the present disclosure.

FIG. 5 illustrates another exemplary method 500 for multiplexed analysis. As illustrated in FIG. 5, the method can comprise acquiring interrogation data using a flow cytometer, the interrogation data associated with a population comprising a plurality of microstructures (510); identifying at least one of a shape, size, and fluorescence of the plurality of microstructures based on the interrogation data (520); and analyzing the population based on at least one of shape, size, and fluorescence of the plurality of microstructures (530). As described above, at least one microstructure in the population can have a different shape than at least another microstructure in the population and comprise a plurality of cells. The method 500 for multiplexed analysis can comprise some or all of the features described above with respect to FIGS. 1-5.

Example Implementations and Results

Various aspects of the disclosed technology may be still more fully understood from the following description of example implementations and corresponding results and FIGS. 6-18b. Some experimental data are presented herein for purposes of illustration and should not be construed as limiting the scope of the disclosed technology in any way or excluding any alternative or additional embodiments.

Example 1

Materials

PEG-based microgels comprised combinations of poly (ethylene glycol) diacrylate (Mw 700 or 3400), 4-arm poly (ethylene glycol) norbornene (Mw 10,000), and 4-arm poly (ethylene glycol) dithiol (Mw 10,000). The photoinitiator used was lithium phenyl-2,4,6-trimethylbenzoylphosphinate (LAP). Solutions were prepared in sterile PBS and filtered before use with a 0.2 μm filter. Fluorescein o-acrylate and fluorescent nano/microparticles (FluoroSphere) were added for fluorescent barcoding measurements. Alginate-based microgels consisted of sodium alginate, sodium chloride, and calcium chloride. SU-8 2010, SU-8 2050, and SU-8 developer were used for wafer patterning.

PDMS Mold Fabrication

AutoCAD was used to design arrays of identical shapes. Twelve microshapes were tested consisting of three different cross-sectional sizes (20, 40, and 60 μm lengths) and four different shapes (square, circle, equilateral triangle, and right triangle). Silicon wafers were spincoated with photoresist according to the manufacturer's instructions. The wafers were exposed through a quartz photomask to 365 nm light and excess unexposed photoresist was removed with developer. PDMS was degassed, poured over the wafers, and cured at 65° C. Cured PDMS was removed from the wafers, cut into individual arrays, and placed on glass slides for handling.

Multiplexing Scale-Up

To determine the total number of multiplexed barcodes, shape, size, and fluorescence were considered separately in the context of the ImageStream. Four shapes were demonstrated here and the remaining shapes are promising additions. Three sizes were demonstrated here, based on the degree of overlap during current fabrication, we think a fourth size could be added. Here, fluorescence was shown in eight of the possible 10 channels. Fluorescent signals could be interpreted easily as "on" or "off" binary states based on an area or signal strength feature in IDEAS. Each of these ten channels could then be combined together to code 210 different materials. However, even with rigorous fluorescence-minus-one (FMO) compensation for spectral overlap, it may be difficult to discern this large number. Instead, it is more realistic to posit 500 different fluorescence barcodes are possible based on the claims of the commercially available Luminex system. Together, these barcoding variables can yield up to 16,000 (from 8*4*500) barcodes.

Fabrication Scale-Up

Figure 6:
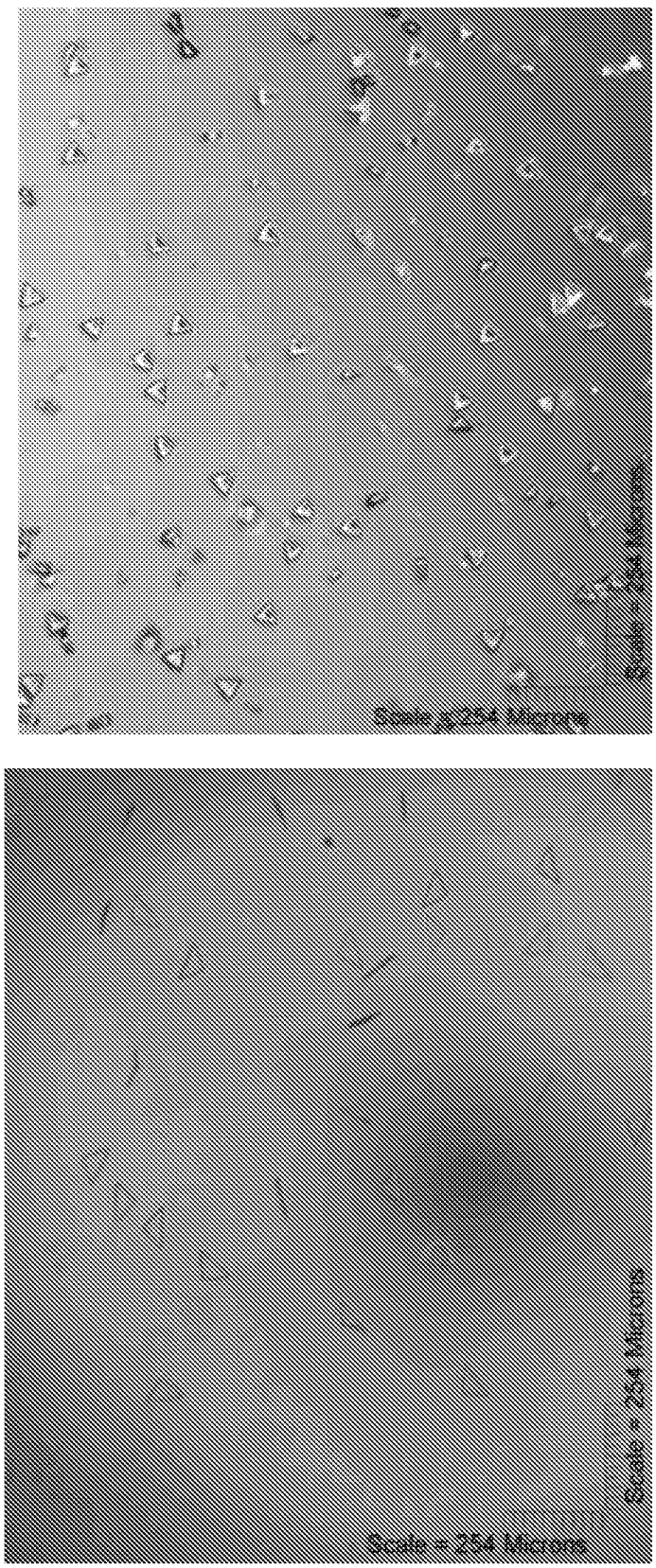
FIG. 6 shows images of two populations of microstructures having different sizes and thickness suspended in PBS after swelling, according to an embodiment of the present disclosure.

Fabrication throughput was scaled up via direct spincoating of prepolymer onto silicon wafers and exposure through a photomask (FIG. 6). FIG. 6 illustrates the ability of microgel generation to be more high-throughput by directly exposing spincoated polymer precursor of controlled thickness to UV light of a photomask. FIG. 6 illustrates two populations of different size and thickness microhydrogels suspended in PBS after spelling. Using a 10 cm wafer and arrays that cover the whole wafer, replicate number can be increased. This increase can enable higher levels of significance (Table 1). For these calculations, the standard deviation of the mean was set to $$p \le \sqrt{\left(0.5 * \frac{1 - 0.5}{n}\right)},$$

and p was calculated for each known n.

from C57BL/6 mouse spleens using the MACS Pan T cell kit and used immediately. Tumor cell-containing microhydrogels were cultured in RPMI media and stem cells in DMEM media, both supplemented with 10% fetal bovine serum and 1% penicillin-streptomycin. Cell-microgel constructs were maintained in a humidified incubator at 37° C. in 5% $CO_2$. Live/Dead staining was performed with a solution of 4 µM calcein AM and 4 µM ethidium homodimer in PBS. Adherent cells were used as a live control and cells treated with 0.1% Saponin-O for 30 minutes were used as a dead control.

Molded Cell-Microgel Constructs

Prepolymer formulations were based on alginate or poly (ethylene glycol). Sodium alginate was dissolved at 1-5% (w/v) in 150 mM sodium chloride solution. PEG-based prepolymer consisted of 10-20% PEG and 0.05-1% photoinitiator in PBS. Each PDMS mold was treated with oxygen plasma to reduce the water contact angle and 5 µL of prepolymer solution was immediately spread on the surface. A pipette tip was used to brush any bubbles from the surface and excess was scraped away with a straight edge. Then the mold was sealed with either an agar block prepared in 100 mM $CaCl_2$ or hydrophobic PDMS (depending on the prepolymer composition) and pressed firmly to isolate polymer into individual microgels. After 2 minutes the agar block was removed from alginate-containing molds and complete media was added to hydrate the microgels. PEG-based microgels were cured by exposure to 365 nm light for 5-120 seconds through the top PDMS layer and released by pipetting in media.

Flow Cytometer Data Acquisition

Microgels were collected by centrifugation and suspended in 100-200 µL of PBS. Samples were run on an ImageStreamX Mark II flow cytometer at the lowest speed and images were analyzed with the IDEAS software. FIG. 9 is functionally descriptive of the ImageStream X Mark II flow cytometer and illustrates the flow of light information from illuminated cells in flow to a TDI CCD camera capable of acquiring images of the illuminated cells. There were few images showing more than one shape passing the interrogation point at the same time ("doublets"); these occurred

TABLE 1

| Mold Type | Array Area (µm²) | Microhydrogel Unit Dimension (µm) | Microhydrogel Mold Area (µm²) | Replicate Number | Level of Significance (p) |
|---|---|---|---|---|---|
| Test 1.5 cm Array | 2.25 * 10⁸ | 20 | 900 | 250,000 | 0.001 |
| | | 40 | 2500 | 90,000 | 0.0016 |
| | | 60 | 4900 | 45,918 | 0.0023 |
| 10 cm Wafer | 78.54 * 10⁸ | 20 | 900 | 8,726,666 | 0.00017 |
| | | 40 | 2500 | 3,141,600 | 0.00028 |
| | | 60 | 4900 | 1,602,857 | 0.00039 |

Cells and Culture Conditions

The A20 B lymphoma cell line (A20s) and human mesenchymal stem cells (hMSCs) (RoosterBio) were used as model cell types. hMSCs were cultured according to manufacturer's instructions and expanded twice before use. Dendritic cells (DCs) were differentiated from bone marrow progenitor cells isolated from C57BL/6 mouse tibias and femurs, and cultured for 7 days in RPMI media supplemented with 10% FBS, 1% penicillin-streptomycin, 100 mM sodium pyruvate, 1% non-essential amino acids, 0.1% 2-mercaptoethanol, 20 ng/mL GM-CSF, and 10 ng/mL IL-4. Media was changed every two days. T cells were isolated mostly in the beginning of the analysis period and were eliminated during analysis. Some cross-contamination was detected between sample runs (slightly decreasing the calculated accuracies for the test dataset) and is estimated by the manufacturer at <0.5% carryover during use of the AutoSampler.

IDEAS Analysis

A training population of at minimum 25 images was defined by eye for each of the twelve tested microparticles (20, 40, and 60 µm lengths for square, circle, equilateral triangle, and right triangle). ImageJ was used for cell viability and loading calculations. Based on feature comparisons, six features defined by IDEAS (Aspect Ratio, LobeCount, Symmetry2, Symmetry3, Symmetry4, and Circularity) were selected as the most effective at separating shape. A seventh feature, mask area, was selected to separate sizes within a shape population.

Figure 7A:
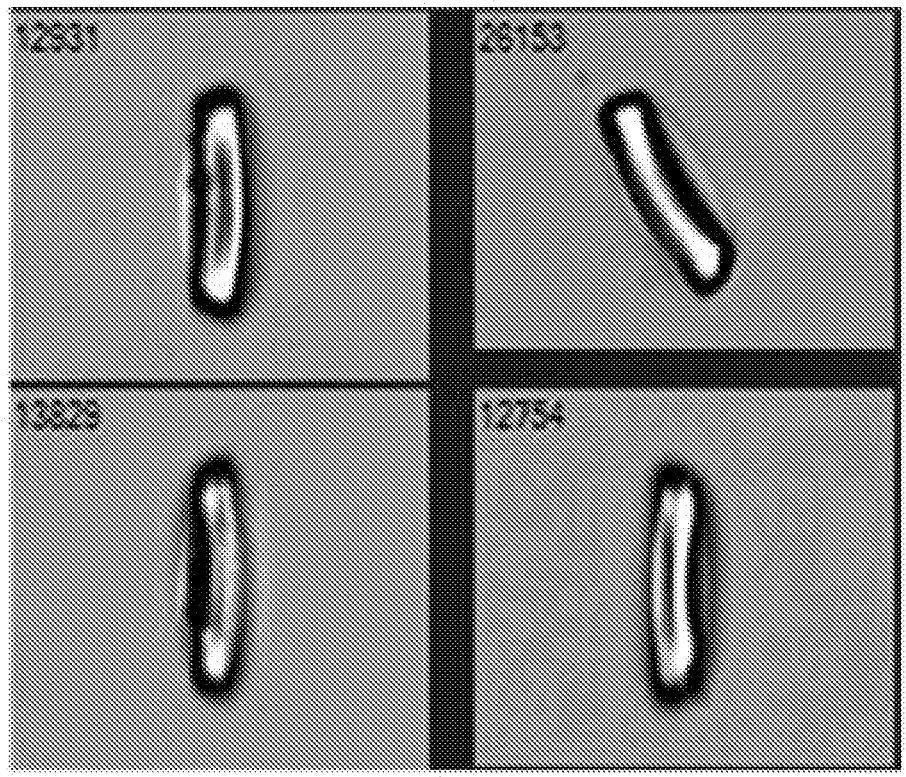
FIG. 7a is an image of microstructures tilted relative to the camera such that the shape barcode cannot be read, according to an embodiment of the present disclosure.

Images with desirable orientation relative to the camera were gated by graphing Area vs. Aspect Ratio and collecting the events with sufficient size for a microhydrogel and a high aspect ratio. Microparticles which tilted relative to the camera would not be distinguishable by shape and were discarded in during collection based on low aspect ratio (FIG. 7a).

Results and Discussion
Test Microhydrogels

Figure 8:
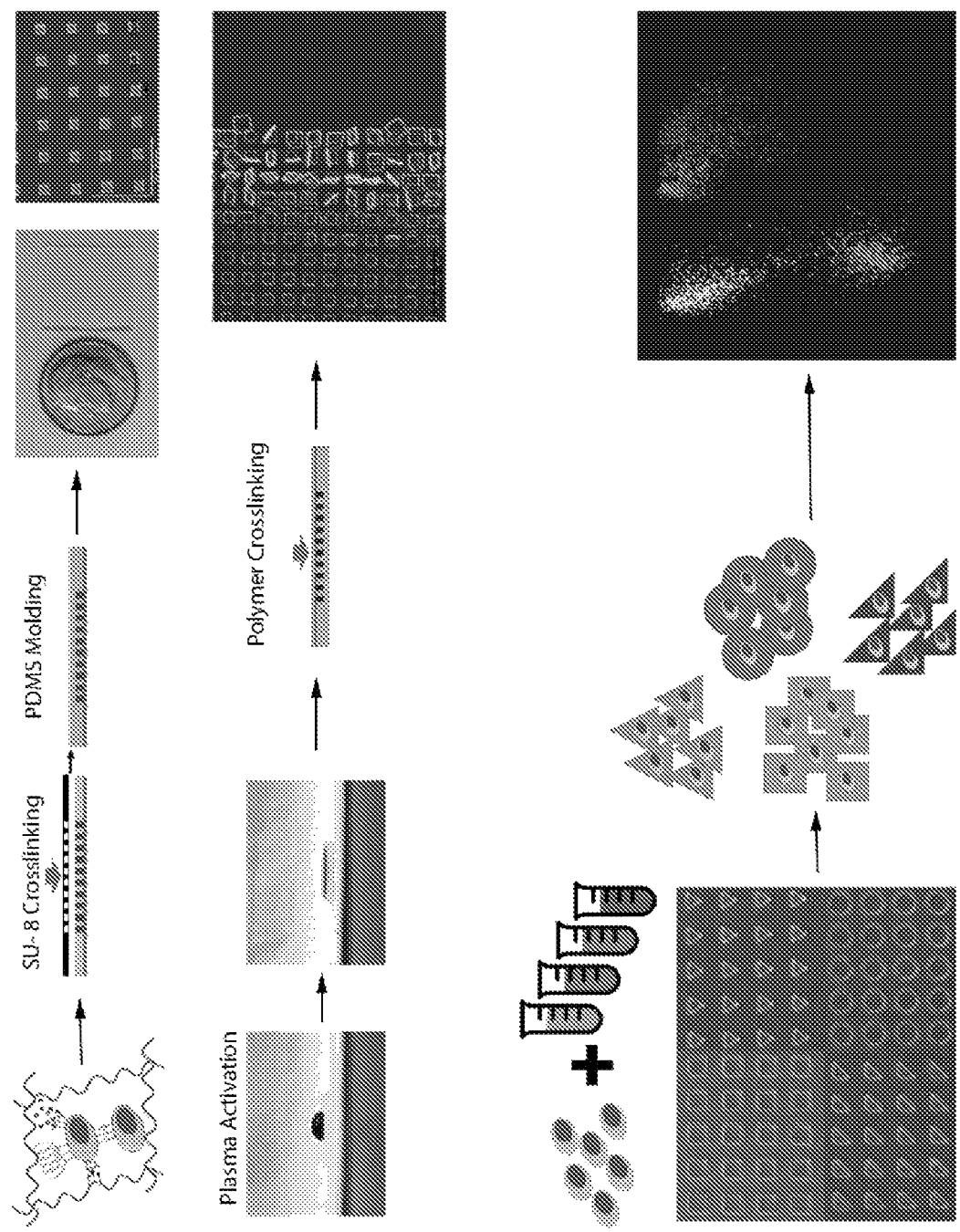
FIG. 8 is an exemplary schematic of microstructure fabrication and testing, according to an embodiment of the present disclosure.

As a proof of concept, twelve tests barcoded microhydrogels were fabricated using soft lithographic methods (FIG. 8). Both alginate and poly(ethylene glycol)-based hydrogels, were tested to demonstrate method versatility. These materials enabled rapid microgel fabrication, liquid suspension handling, and are easily chemically modified. High "n" was achieved by using arrays of >$10^4$ molds per 2 μL of precursor; tens of thousands of replicate viable cell-laden gels were produced and harvested (overall process, FIG. 8). For each starting volume of 2 μL of prepolymer, the average number of collected microgels was 3500. When scaled to a 20 μL starting volume, this number of microgels jumped to 49,200, showing that collection efficiency was slightly higher with higher volumes. FIG. 6 and Table 1 above show how the number of replicates for each microgel type (barcode) can be increased further to >$10^6$ using conventional whole wafer printing.

Cell Populations and Processing 3D niches containing cancer or stem cells were chosen for exploratory studies. Both cell types have heterogeneous populations and a behavioral dependence on encapsulating material; and would therefore benefit from population-level statistics gathered from individual events. In stem cell research, the starting population can demonstrate a range of responses to identical material and stimuli, and in cancer research in vivo behavior is best mimicked when tumor cells are co-cultured with supporting cells in an appropriate material niche.

Figure 10A:
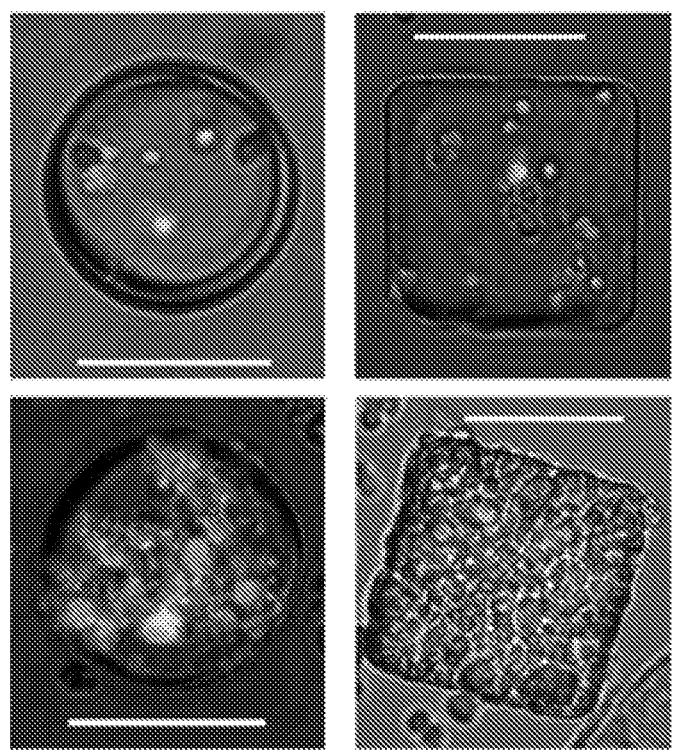
FIGS. 10a-10d show various images and graphical representations indicative of cell incorporation into microhydrogels, according to an embodiment of the present disclosure.
Figure 10B:
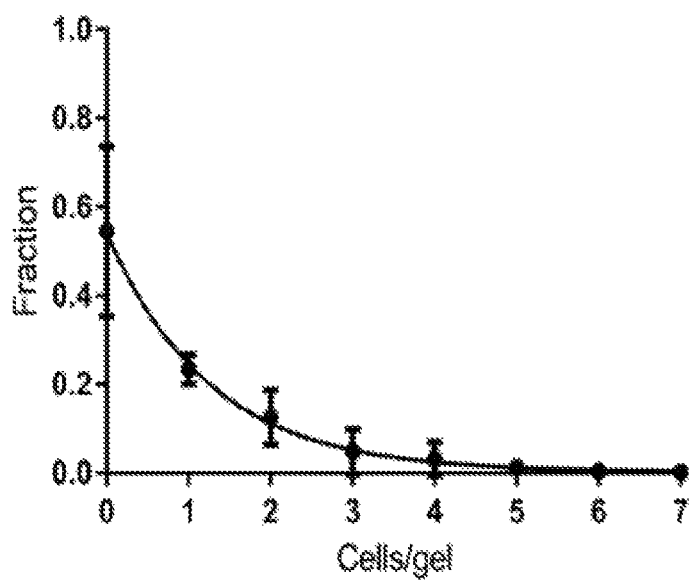
Figure 10C:
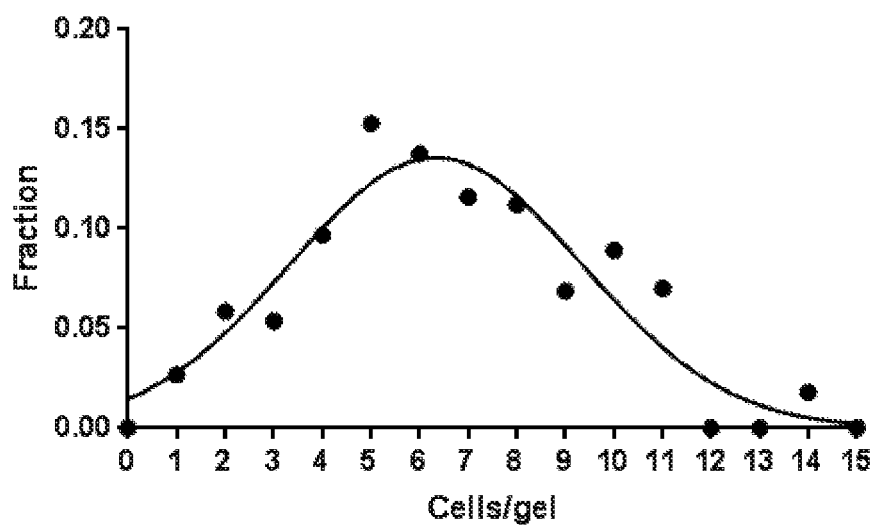
Figure 10D:
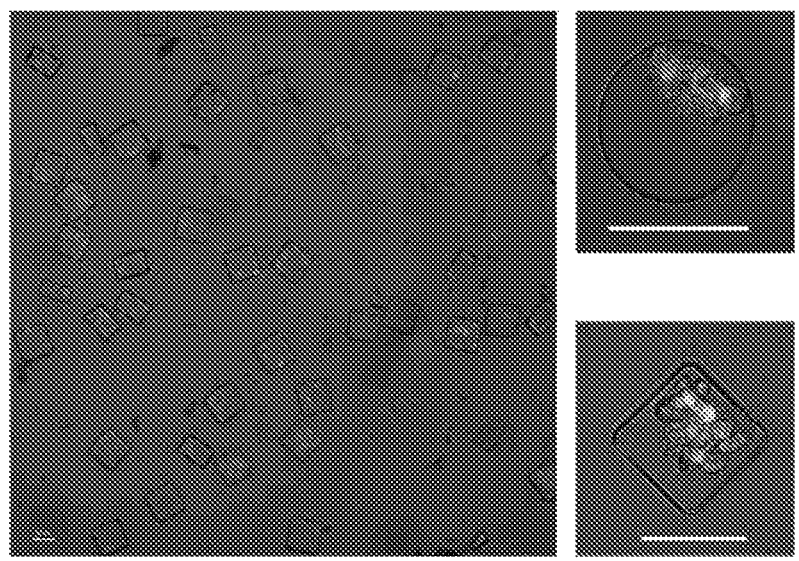

A wide range of cell densities could be achieved in the selected microhydrogel geometries, which is an important variable in cell-niche interaction studies (FIG. 10a). FIG. 10a illustrates exemplary microenvironments constructed with sparse or dense cell packing model of different microenvironments. Lower cell concentrations ($10^5$ cell/mL) mimic single biomaterial-cell interactions within the niche and higher cell concentrations ($10^6$-$10^7$ cell/mL) could be used to mimic organoids or tissue microenvironments. For each of the stated concentrations the number of cells per microhydrogel was quantified using fluorescence microscopy and ImageJ. For the lower concentration more than 200 wells were counted and for the higher concentration more than 185 were counted. FIG. 10b shows the low concentration case as a number average to demonstrate the proportion of wells that were filled in each case. For the higher concentration case (FIG. 10c), a weighted average is shown instead to demonstrate in what size community each cell is most likely found. Fluorescent images of stained cells were collected and ImageJ used to quantify live and dead cells (for a total of more than 550 cells). This confirmed that cells remain viable post-gelation (FIG. 10d) with approximately 80.2% viability 24 hours after crosslinking. For FIGS. 10a and 10d all scale bars are 50 μm and 100 μm, respectively.

ImageStream Data Collection and Barcoding

Figure 11A:
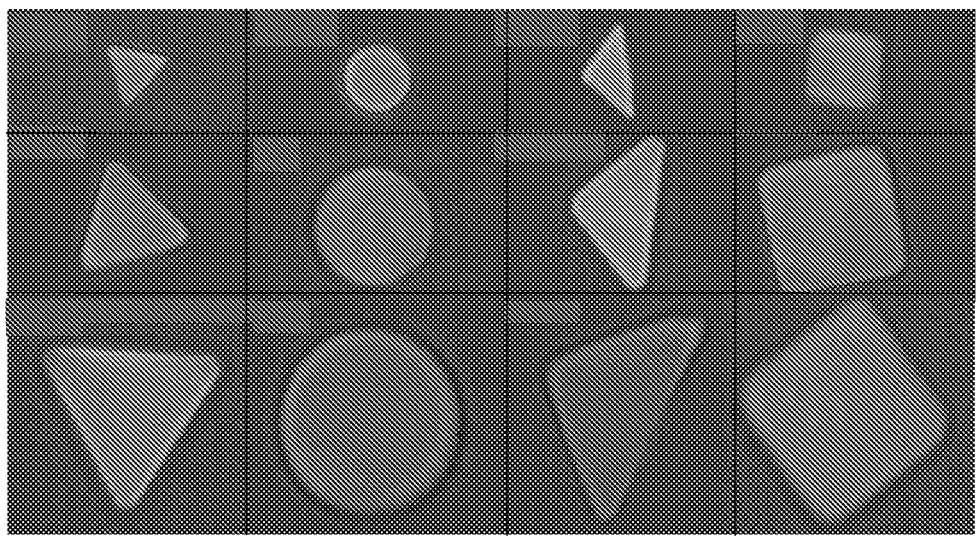
FIGS. 11a-11c show various images illustrating microhydrogel barcoding, according to an embodiment of the present disclosure.
Figure 11B:
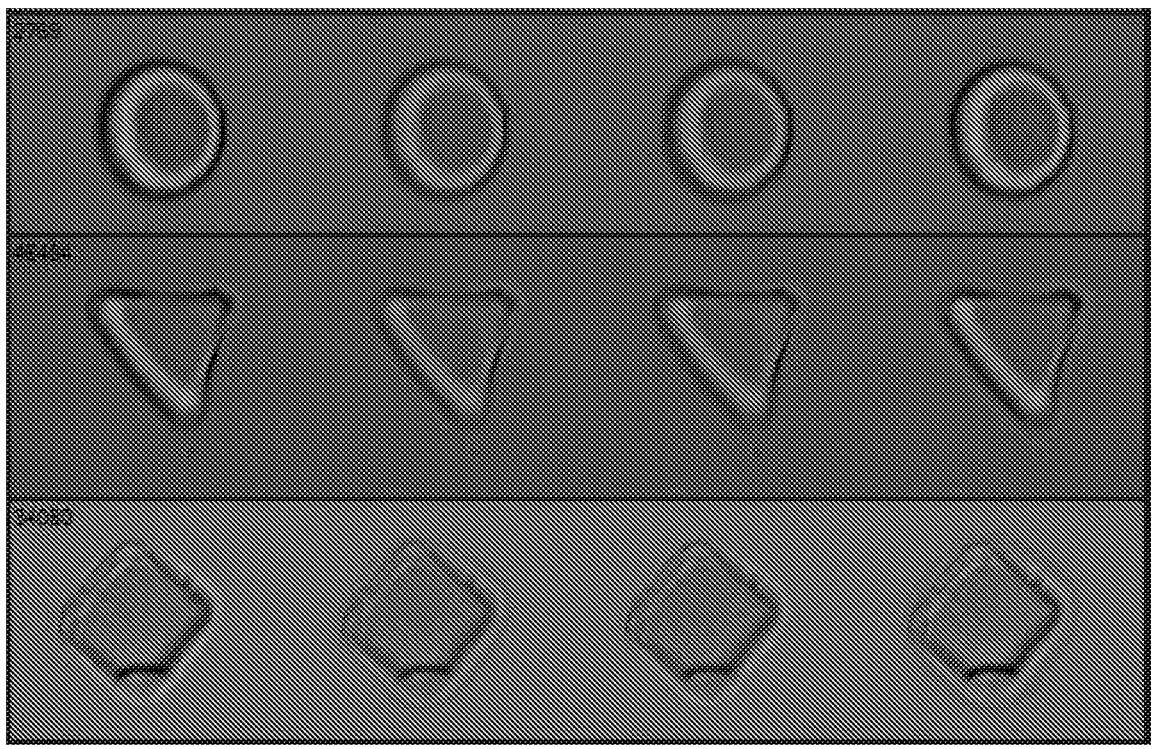
Figure 11C:
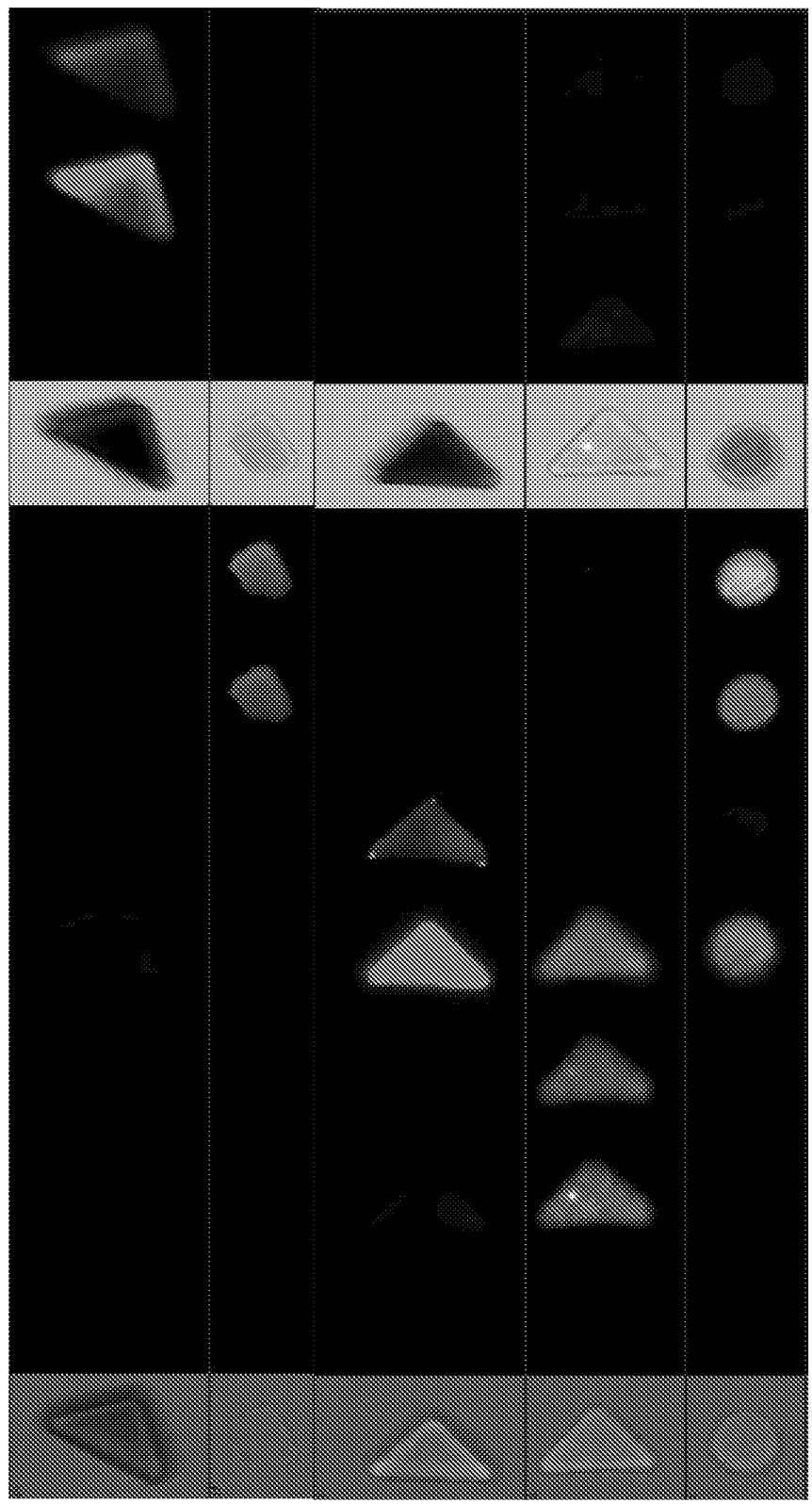

Representative bright-field images collected by the ImageStreamX flow cytometer for each of the test barcodes are shown (FIG. 11a). The pre-defined shape and size barcodes are clearly identifiable in collected images and undesirable images were discarded based on area and aspect ratio (FIG. 7a). To quantify the barcodes, masks were drawn on the brightfield image (FIG. 11b) and greater than 75 features calculated for each image. To further increase the degree of multiplexing, microgel prepolymer were mixed with fluorescent dyes visible in up to ten different channels (the maximum of the ISX). Microhydrogels were tagged in various combinations to demonstrate, as proof of concept, six possible codes that could be layered with the shape/size signature (FIG. 11c).

Based on the sensitivity of the ISX to the chosen SSF barcoding, the estimated number of barcodes available would be greater than 300 (Table 2). By using the 10 fluorescent channels in combination, a theoretical $2^{10}$ fluorescent barcoding indices are possible with the application of established compensation protocols, which would potentially expand the number of barcodes significantly. However, a more reasonable estimate is the 500 combinations already demonstrated by the Luminex system. Each additional color used in barcoding removes a fluorescence channel that could be used for detection, but adds another multiplexing variable. Similar to a Luminex system, relative fluorescence intensity could further expand the number of available barcodes.

TABLE 2

| System | Parameters | | | Total |
| --- | --- | --- | --- | --- |
| | Cross-Section | Size | Fluorescence | Multiplexing |
| ImageStreamX (ISX) | Square, Circle, Right Triangle, Equilateral Triangle, Rectangle (2x, 3x, 4x), Pentagon | 20, 40, 60, 80 μm →4 | 10 Channels 500 Compensated Combinations | Over 300 ~16,000 |
| BD LSR Fortessa (LSR) | Square, Circle, Triangle, Rod | 25-75 μm | 18 Channels | Up to 216 |

IDEAS Data Analysis

Figure 7B:
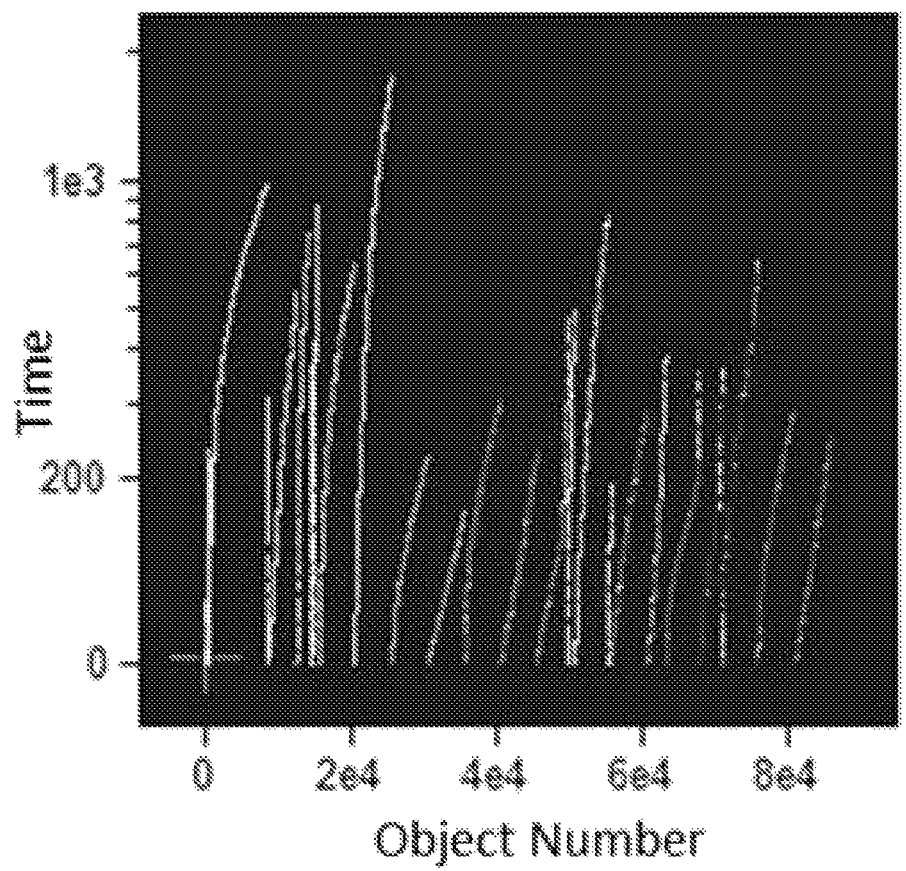
FIG. 7b is a scatterplot of all sample runs showing similar data collection rates across samples, according to an embodiment of the present disclosure.

Data were analyzed using the IDEAS software. An analysis template was defined from microgels of known SSF barcode ("truth populations") and data collection rates were shown to be consistent (FIG. 7b). Similar to traditional gating methods, data could be plotted according to user-chosen parameters, subpopulations identified, and the data further defined. For each shape, true populations were compared to extract features which give the greatest separation between groups. Similar to the shape and size gating, fluorescence signatures could be quantified using several of the IDEAS values. From these measurements, the Area and Max Pixel Intensity variables were selected for the highest accuracy separation of the fluorescent barcodes. Additionally, calibration beads were used as a proxy for cells and run at different concentrations to develop a spot counting template. The selected features for the beads were (in order) Symmetry2, Aspect Ratio Intensity, Major Axis Intensity, and Symmetry4. However, when counting actual CFSE-labelled cells with DAPI-labelled nuclei, instead the principle components were (in order) SpotCount, Major Axis Intensity, Perimeter Threshold, Compactness, Shape Ratio, and Symmetry2. IDEAS also defaulted to using the strong CFSE staining over the relatively weaker DAPI staining to count and define the different number of cells.

Figure 12B:
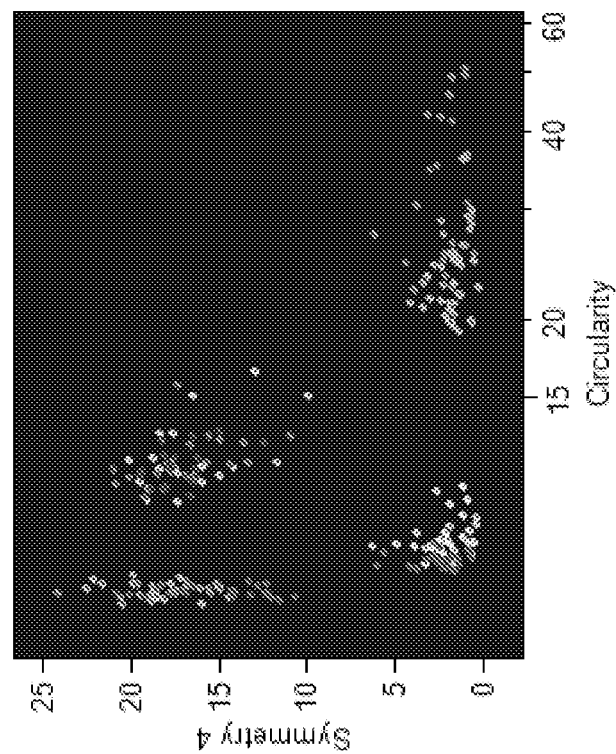
FIGS. 12a-12c are various graphical representations of true populations used to define four shapes and three sizes of microhydrogels, according to an embodiment of the present disclosure.
Figure 12A:
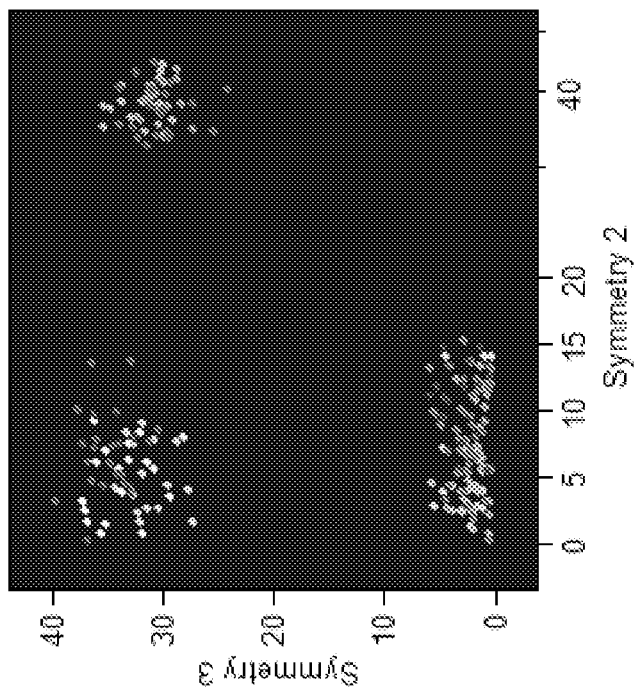
Figure 12C:
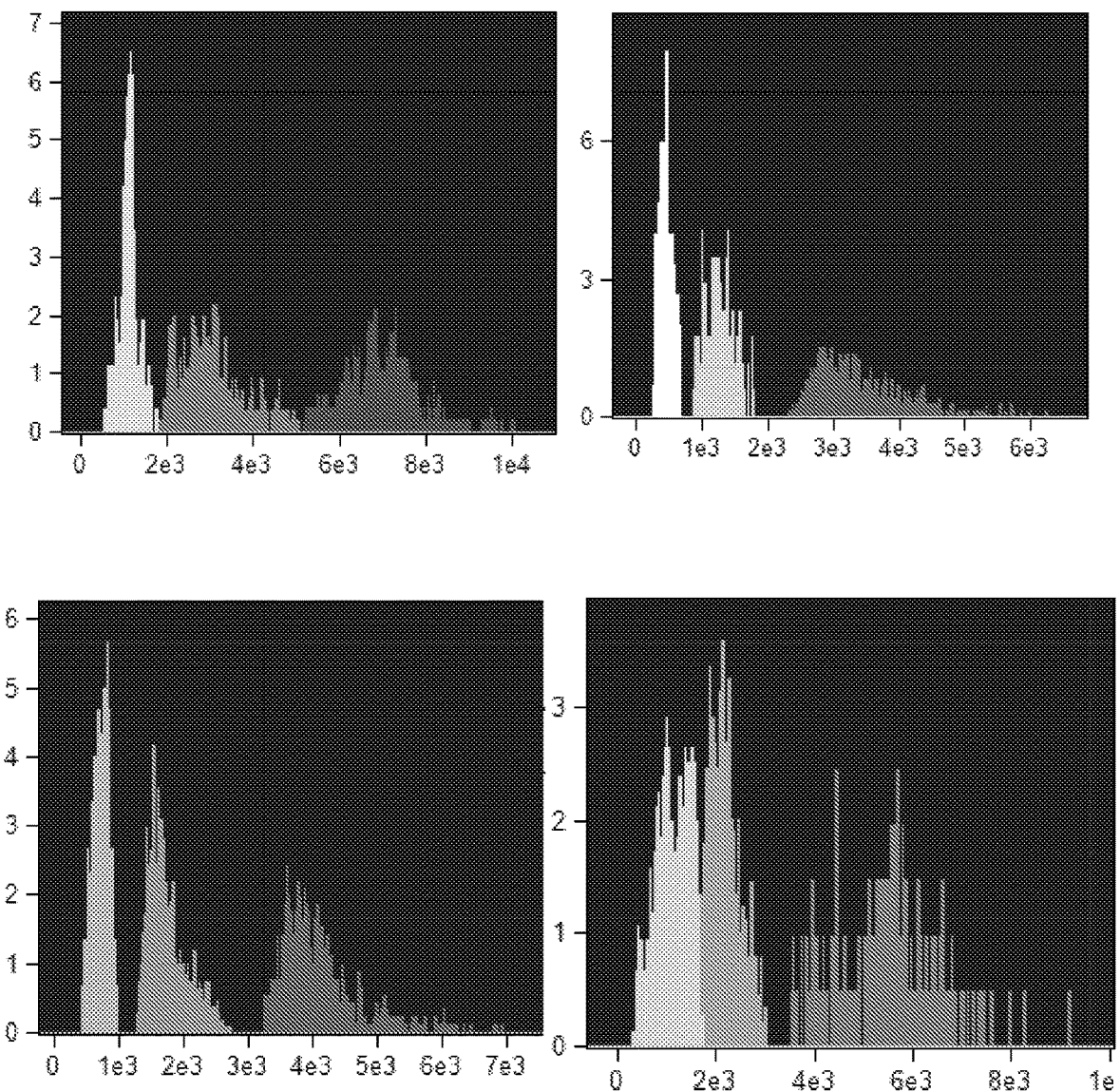
Figure 13:
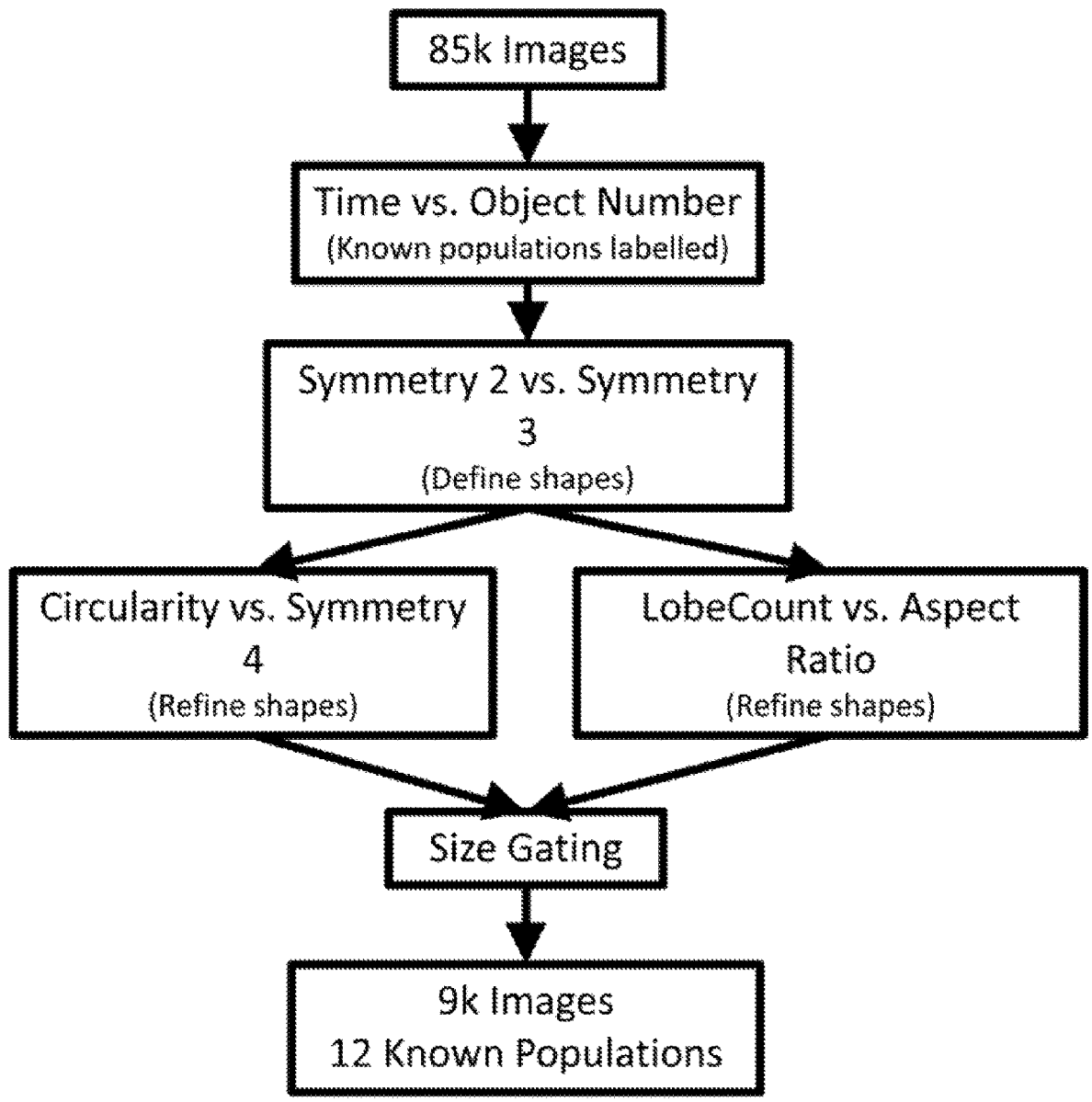
FIG. 13 is a flow diagram for analysis used to define a gating template, according to an embodiment of the present disclosure.

This template was applied to a test dataset of over 85,000 events and graphed. Both triangular shapes separate on two features but the squares and circles are overlaid (FIG. 12a). Additional gating was applied to generate FIG. 12b and FIG. 12c (full scheme, FIG. 13). FIGS. 12a-12c show plots of true populations used to define the four shapes and three sizes of microhydrogels (Right Triangle-purples, Triangle-greens, Squares-blues, Circles-reds). FIG. 12a shows preliminary shape gating using two features shows three populations (top-left being triangle, top-right being right triange, and the bottom grouping showing overlapping squares and circle populations). FIG. 12b shows an additional two features defines all four shapes present in the system (top-left being right triange, top-right being squares, bottom-left being triangle, and bottom right being circles. Histograms of the area feature for each shaped population can be gated by size to define all twelve barcodes, as illustrated in FIG. 12c.

For each shape subpopulation, an area histogram shows three distinctly sized subpopulations gated such that the twelve barcodes are defined in the dataset (FIG. 12c). The IDEAS gating achieves an average accuracy of 82% for all twelve populations and an average of 88% for the 40 and 60 µm populations (Table 3). Once designed, this sorting template can be applied directly to new datasets for automated identification of barcoded populations similar to traditional flow cytometry. Therefore, IDEAS-based analysis is scalable with regards to dataset size, and a single experiment could be performed and analyzed within a single day.

TABLE 3

| Size | Circle | Right Triangle | Square | Triangle |
|---|---|---|---|---|
| 20 | 41.38% | 62.67% | 86.97% | 92.05% |
| 40 | 80.88% | 84.60% | 75.91% | 80.92% |
| 60 | 94.61% | 88.38% | 97.89% | 99.05% |

This example demonstrates a high replicate, high throughput system for biomaterial analysis using imaging flow cytometry. Greater than 85,000 events were collected and gated with high accuracies into the constituent 12 test barcodes of shape and size. The image analysis based on radius-basis and frequency domain feature distinguished the convex shapes used in this study and the nonlinear t-SNE visualization of the frequency features provides an excellent opportunity to classify shape via manual gating. As in traditional flow cytometry gating schemes, a balance is struck between accuracy and throughput; generally one route is chosen depending on the needs of the experiment. In the future, if new shapes are included in the population, the analysis can be extended. The classification performance can be further improved by enhancing the preprocessing pipeline's ability to exclude low quality images.

By combining all samples into a pooled population, both material- and cell-based variables should be better standardized to reduce variation between experimental conditions. Based on the sensitivity of the ImageStreamX, the estimated total number of barcodes that could be designed to designate different material compositions would be greater than 300. Each additional color used in barcoding would occupy a fluorescent channel that could otherwise be used for detection, but adds another multiplexing variable. Similar to the Luminex labeling system, relative fluorescence intensity could further expand the number of available barcodes.

The method was applied to biomaterial scaffolding microparticles but is equally applicable to other HTS targets such as analyte-sensing microparticles. Most excitingly, current non-imaging flow cytometers have the ability to physically sort microparticles (FACS) based on user-designed gating schemes such that individual events are separated out of the population and collected for further manipulation and analysis. Biomaterials screening could then be applied to translational work as encapsulated cells are cultured, analyzed, and then only the highest performing constructs selected for implantation. As imaging flow cytometer technology continues to improve and as imaging flow cytometers enter wider circulation, this biomaterial barcoding scheme can be expected to continue to gain utility.

Figure 14:
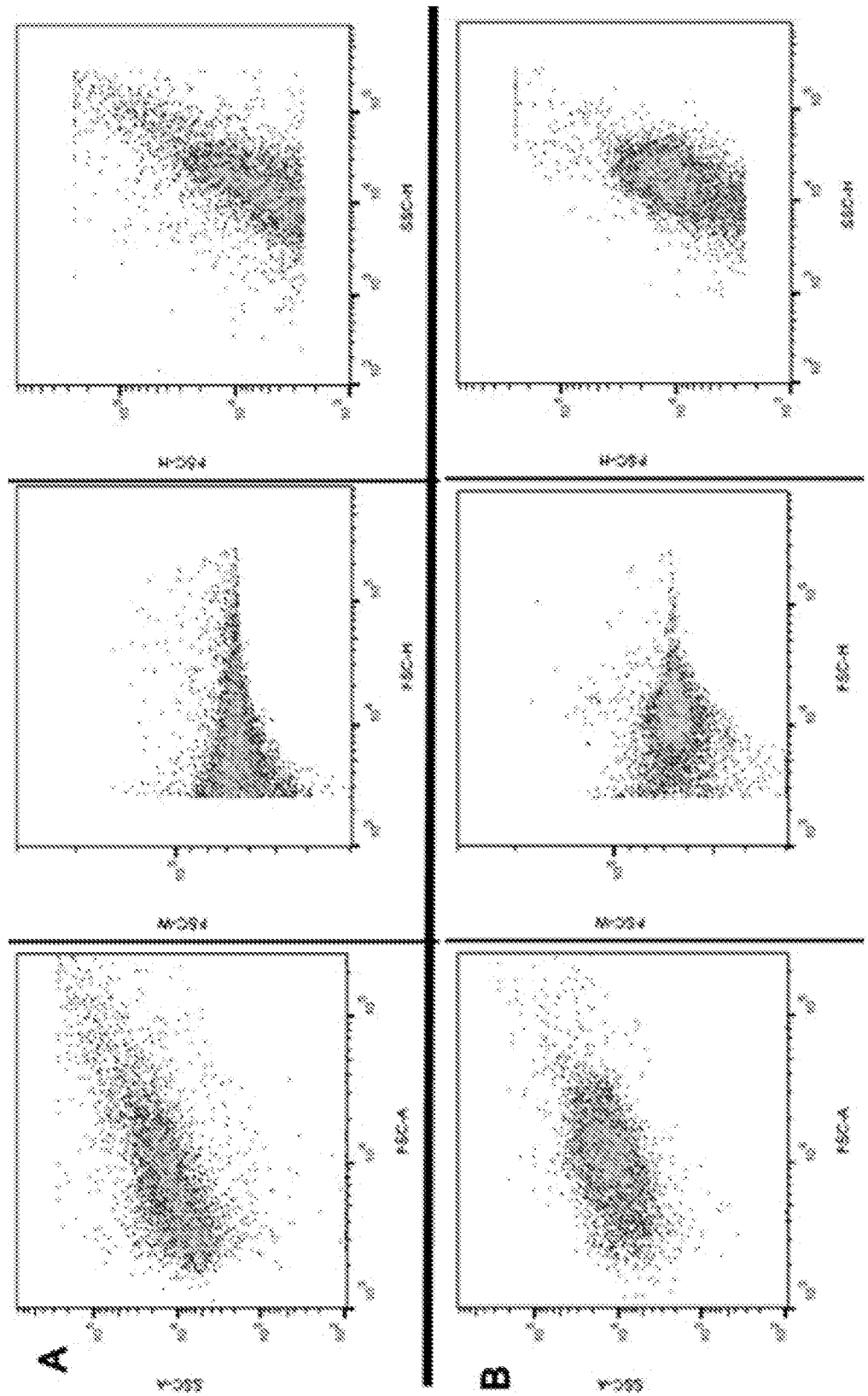
FIG. 14 illustrates results for non-image flow cytometry analysis, according to an embodiment of the present disclosure.

Non-imaging flow cytometers, such as the BD LSR Fortessa used here, can also benefit from additional barcodes based on shape-multiplexing. Here a small shift can be seen in FSC versus SSC scatterplots between 20 mm (A) and 40 mm (B) cross-sectional microparticles, as seen at FIG. 14.

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. The patentable scope of certain embodiments of the disclosed technology is indicated by the appended claims, rather than the foregoing description, and all changes that come within the meaning and range of equivalents thereof are intended to be embraced therein.

Example 2

Methods

Microgels were fabricated from prepolymer formulations comprising Poly(ethylene glycol) 5-20% PEG-diacrylate (MW 700)+10-40% PEG (MW 600)+0-20% PEG$_{400}$monomethacrylate+0.1-2% photoinitiator+0.3% NVP accelerant, 1-5% sodium alginate, and ~$10^6$ cells/mL. PDMS molds of the desired microshapes (square, circle, right triangle, equilateral triangle) were created to fabricate microgels of varying thickness (5 to 30 µm) and length (20, 40, and 60 µm) using a 150×150 elements per array. Poly (ethylene glycol) was cured under 365 nm light at 10 mW/cm$^2$ for 5-45 seconds and alignate was cured by contact with a 100 mM CaCl$_2$-infused agar slab for 2 minutes.

Analysis was performed using an ImageStream Mark II flow cytometer. A minimum of 12 parameters calculated for each image, ranked according to their ability to distinguish two training populations. Separation was performed based on 14 gates defined for 12 test gels with high-throughput capability of 320 events per µL.

Results of Cell Encapsulation

Figure 15A:
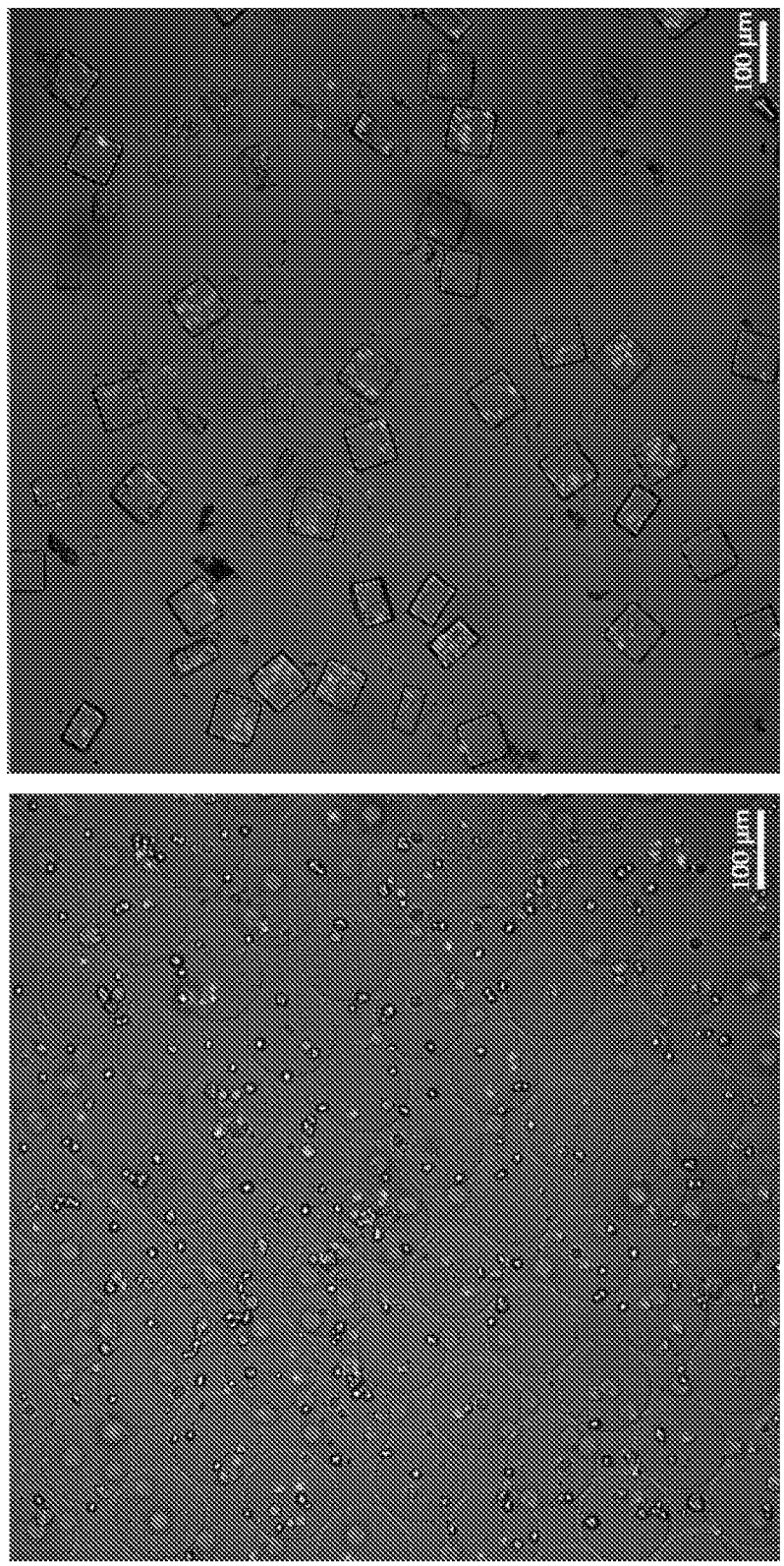
FIGS. 15a-15c illustrate various images and graphical representations showing cell encapsulation within microstructures and viability of cells within microstructures, according to an embodiment of the present disclosure.
Figure 15B:
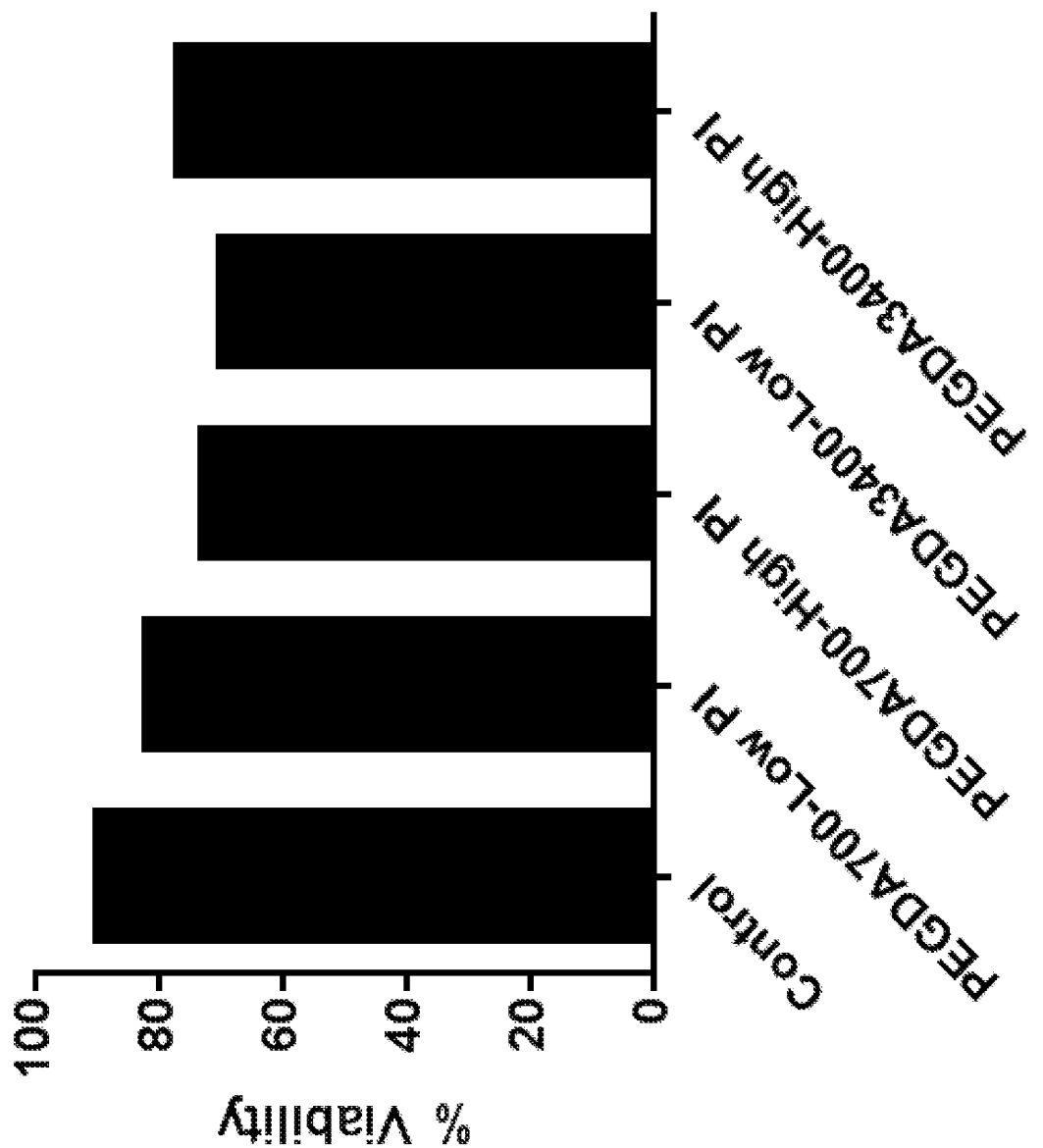
Figure 15C:
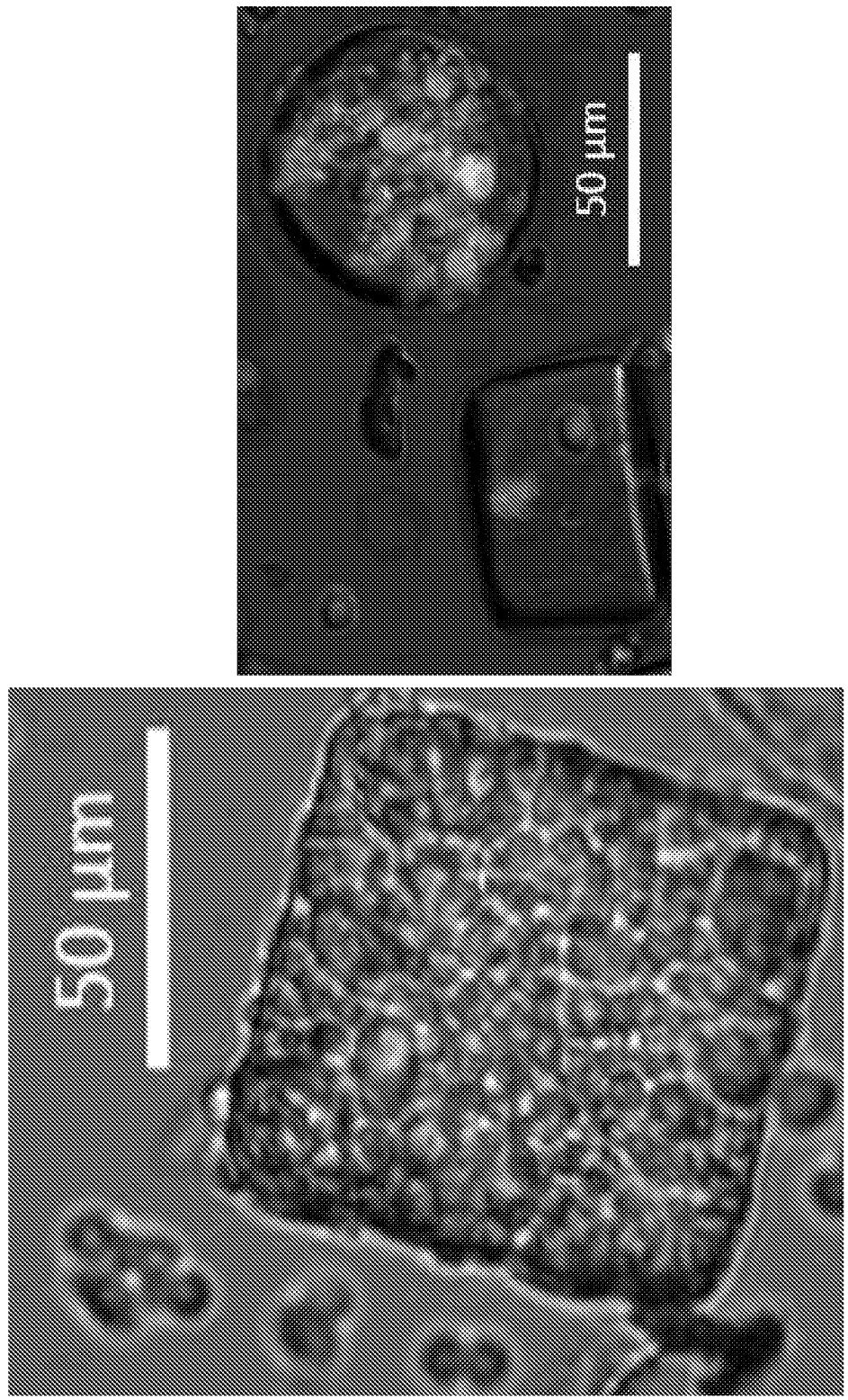

FIG. 15a shows fluorescent images of cell viability, adhered to coverslip and released in solution. FIG. 15b shows cell viabilities after 30 minutes suspension in pre-polymer quantified via trypan blue staining. FIG. 15c show multiple cell types pre-stained and encapsulated at high density to form microenvironments.

Results of Gating

Figure 16A:
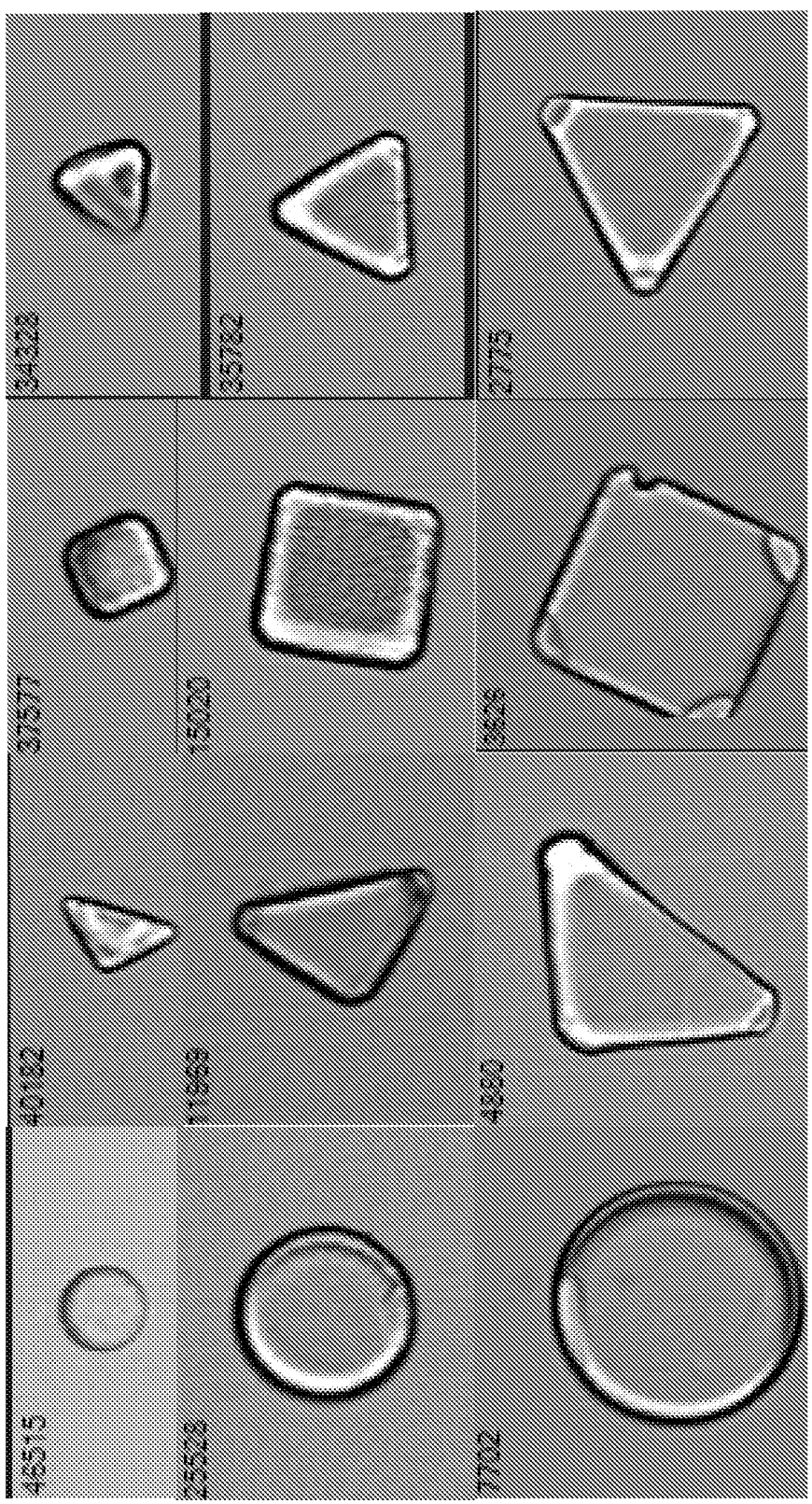
FIGS. 16a-16c illustrate various images of microstructures and graphical representations demonstrating sorting of microstructures, according to an embodiment of the present disclosure.
Figure 16B:
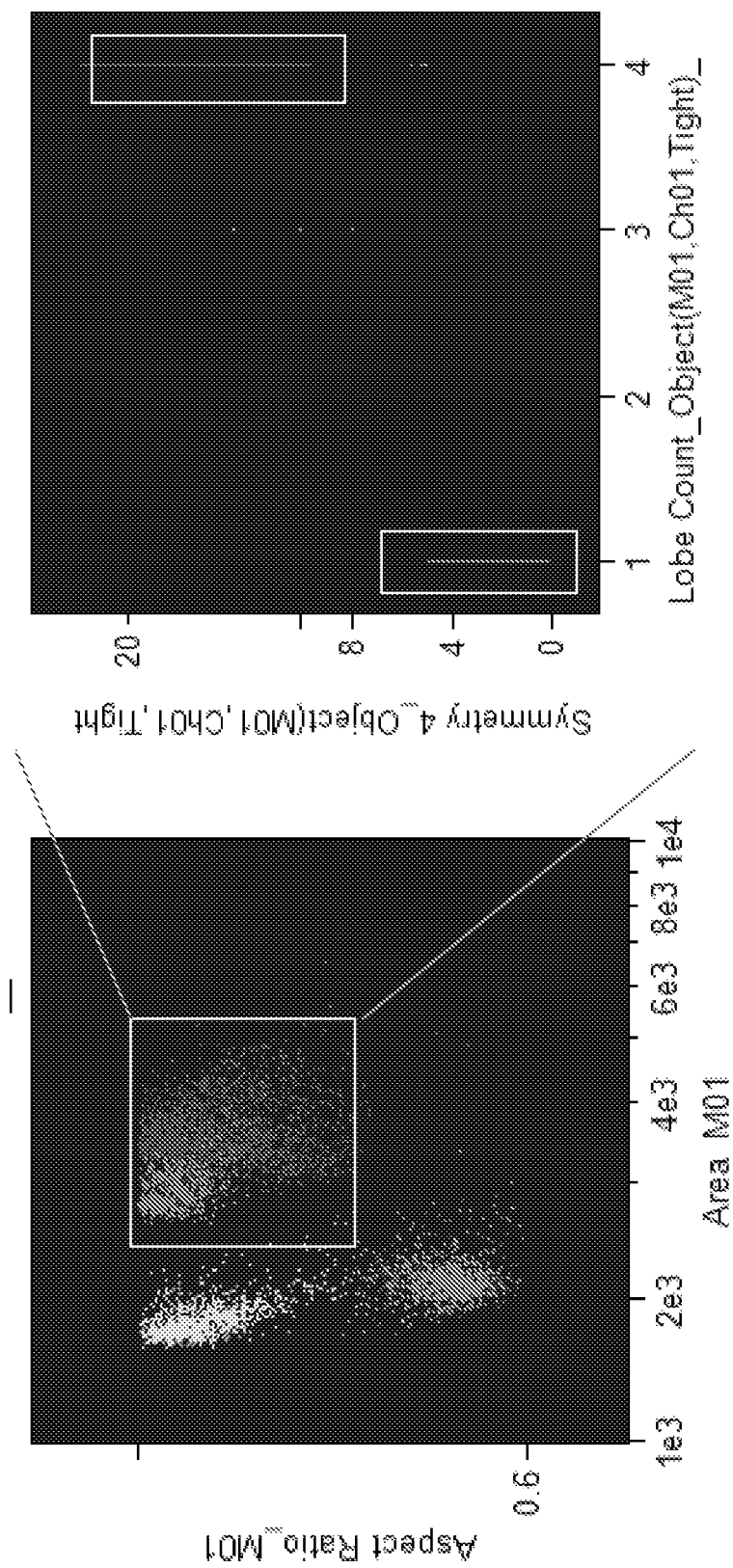
Figure 16C:
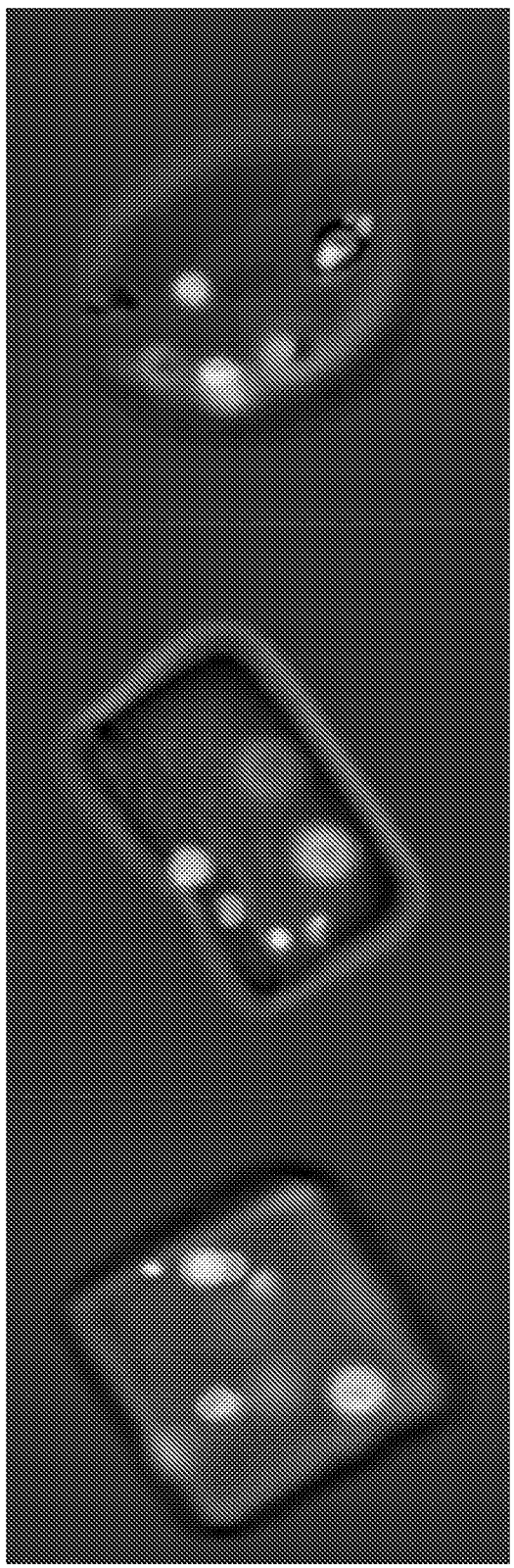

FIG. 16a shows representative images of the test microparticles as captured by the ImageStream. FIG. 16b shows color-coded subpopulations showing the high purity of the sorted shapes based on calculated area and aspect ratio (Red-circle (top middle), blue-square (top right), green-equilateral triangle (top left), purple-right triangle (bottom left). A second gating results in completely separated subpopulations. FIG. 16c shows images of cell-containing 60 µm microparticles in the ImageStream (bottom left-red and top right blue). Table 4 below shows gating success percentages for test 40 µm microparticles

TABLE 4

| Size | | Circle | Square | Right Triangle | Equilateral Triangle |
|---|---|---|---|---|---|
| 40 µm | # Gated Shapes | 1095 | 2297 | 1386 | 1205 |
| | # Incorrect | 9 | 43 | 75 | 79 |
| | Success | 99.2% | 98.1% | 94.6% | 93.4% |
| 60 µm | # Gated Shapes | 180 | 53 | 506 | 382 |
| | # Incorrect | 1 | 7 | 16 | 28 |
| | Success | 99.4% | 86.8% | 96.8% | 92.7 |

PEGDA and alginate-based microgels could be shaped into cell-containing microgels permissible for flow cytometry. User-defined gates can be drawn in the IDEAS analysis software for the ImageStream Mark II to separate microgels with high purity Example 3

Methods

Tumor cells and tumor-supporting cells such as fibroblasts, monocyte-derived suppressor cells (MDSCs), Treg and effector T cells, and macrophages can be encapsulated in microstructures. Specifically, tumor/stromal cells can be isolated from in vivo established A20 B-lymphomas, which mimics DLBCL in mouse models. In vivo isolated tumors can be used to better mimic the tumor microenvironment effects. To study effects of tumor cells on other stromal cells and vice versa, while varying the tumor cell-stromal cell ratios, tumor cells can be flow corted from in vivo isolated tumors and then "add-in" primary macrophages, T cells or MDSCs isolated from the spleen of the same animal. The following types of cells can be co-encapsulated with the tumor cells: CD11b+Gr-1/Ly-6G+ MDSCs, CD4+Foxp3+ Treg cells, CD4+ and CD8+ T cells, CD11c+ DCs and CD11b+F4/80+ macrophages (all from spleen), and dermal skin fibroblasts.

First, photolithography can be used to crosslink the desired shapes in photoresist on silicon wafers by exposing the SU-8 to 365 nm light through a photomask. The exposed wafers are then cured on a 100° C. hotplate for 1 minute and developed for 3 minutes to remove un-crosslinked photoresist, leaving the desired microshapes on the silicon wafer. Wafers are coated with a 10:1 mixture of PDMS pre-polymer and curing agent, placed under vacuum to remove bubbles, and heated to 60° C. for two hours to cure. To demonstrate the high-throughput nature of our process a sample PDMS mold which consists of an array of 300×300 shaped imprints with dimensions of 1.5×1.5 cm; this number can be increased by orders of magnitude to reach any desired number of replicates with a single 10 cm diameter wafer producing up to $3 \times 10^6$ microgels with 20 µm dimensions. Test microgels may have dimensions of 20, 40, 60 and 100 µm dimensions with a range of thicknesses.

A pre-hydrogel solution is made by mixing sterile-filtered 150 mM NaCl and 1-3% (w/v) alginate, +/- various ECM components as discussed before (1-10% w/v collagen and fibronectin; 1-2% w/v HA). PEG-based prepolymer consists of 10-20% PEGDA700, 40% PEG600, 2% photoinitiator, 0.3% NVP accelerant, and ECM components. This prepolymer mixture can be chosen based on its known porosity and accessibility of proteins as large as 500 kDa. Cells can be added to the pre-hydrogel solution for a final concentration of $10^6$ cells/mL such that each micro-hydrogel incorporates the desired ratio of tumor and tumor-supporting cells. Fluorescent "bar codes" can be incorporated into the microgels by adding 2% fluorescein-alginate/acrylate, and rhodamine-alginate/acrylate. The cell-laden prepolymer can then be pipetted onto the PDMS mold (which was pre-treated with oxygen-plasma for 45 seconds for hydrophilicity). After letting the cells settle into microwells, a cover slip can be used to gently remove the excess alginate pre-polymer or PEG-based prepolymer is sealed into the wells by application of a piece of hydrophobic PDMS. This can prevent a scum layer from forming, thus eliminating any subsequent etching need. An agar block prepared with 100 mM $CaCl_2$ can then applied with gentle pressure to seal the alginate pre-polymer/cell mixture into the molds and allowed 2 minutes to gel. The agar block is removed and complete media is added to the mold in order to hydrate the microgels and a pipet is used to gently "tap" and suspend them in solution. PEGDA-based microgels are cured by exposure to 365 nm light for 30 seconds and then released by pipetting. Cell-microgels can be maintained in RPMI culture media containing 10% FBS. The mechanical properties of alginate gels were tuned by controlling the weight % and $Ca^{2+}$ crosslinking concentration, and the same has been done in PEG-based systems by varying molecular weight and weight percent.

To obtain estimates of the reproducibility and variability of our system, particles can be characterized using microscopy to quantify their final shape and size. Average and standard deviation values can be calculated for each population produced. Cell encapsulation in the microgels can be evaluated as well; staining each population of cells with different intracellular stains (e.g. CFSE) prior to co-encapsulation so they can be easily identified by fluorescence microscopy. In order to evaluate the condition of the cells, fluorescence microscopy can be used to determine live/dead percentages and proliferation (Calcein/Ethidium live/dead assay, Life Technologies. Proliferation assays can be performed by using a CFSE dye dilution assay, dissolving the microgels (using competing Na+ ions or collagenase/hyaluronidase treatments) and assessing proliferation through typical flow cytometry assays. Clonogenicity assays can be performed by culturing a small number (one-two, by reducing cell concentration in the pre-polymer) of cells per microgel and evaluating their ability to form a colony of at least 50 clones. To evaluate whether cells can be stained with antibodies within the microgels, cells can be fluorescently labeled anti-CD19 (for B cells/tumor cells) and anti CD4 (for effector and regulatory T cells), as an example. All these assays may be repeated at the following relevant time points for a A20 tumor: in pre-polymer solution, immediately post-gelation, and every 24 h for 5 days.

Results

Figure 17:
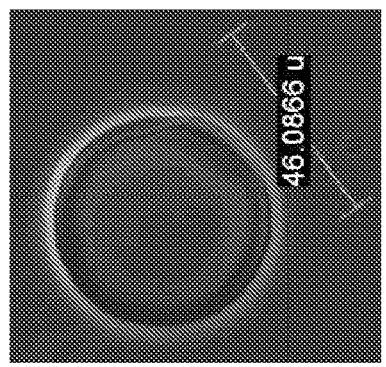
FIG. 17 are images showing released alginate microparticles showing fidelity to mold and released PEGDA micro-particles showing swelling and monodispersity, according to an embodiment of the present disclosure.
Figure 17:
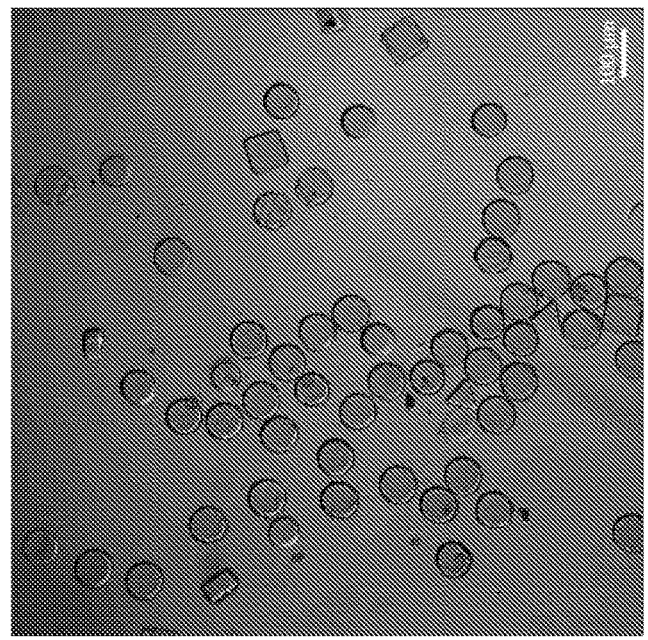
Figure 17:
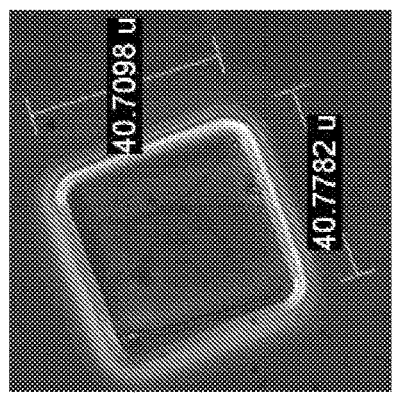
Figure 17:
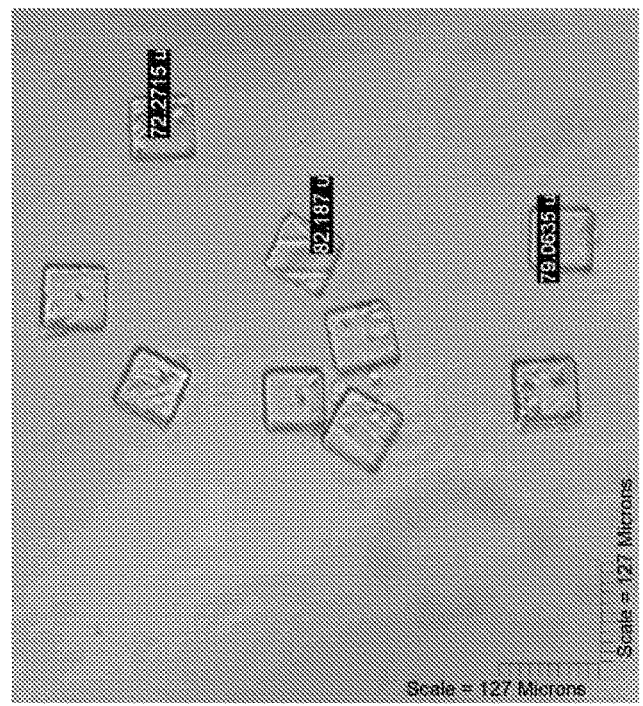

FIG. 17 illustrates the ability to successfully fabricate shape and size-specific alginate and PEGDA hydrogels, and release them in solution via swelling. Collagen IV, fibronectin and hyaluronic acid can be used as potential ECM materials to incorporate within the microgels, since these are typical in tumor microenvironments and often implicated in pathogenesis. They can also contribute to components of the Diffuse large B-cell lymphoma (DLBCL) niches.

Figure 18B:
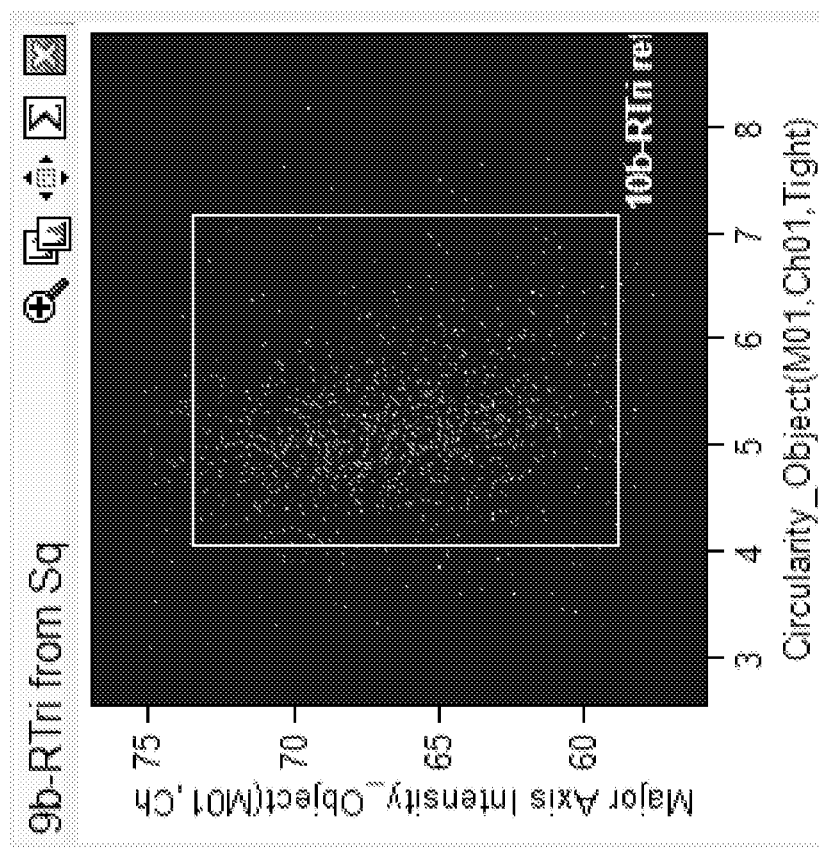
FIGS. 18a and 18b show graphical representations illustrating color-coded subpopulations showing high purity of sorted microstructure shapes, according to an embodiment of the present disclosure.
Figure 18A:
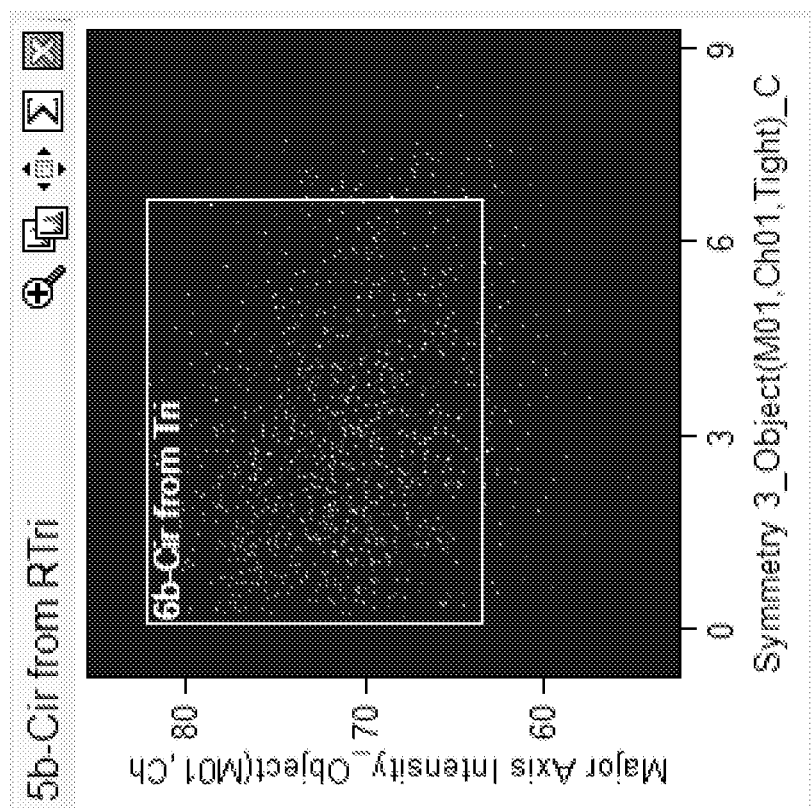

Shapes are distinguishable when run in an imaging-based flow cytometer by image and a gating scheme can result in high purity subpopulations (FIG. 18a, 18b).

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based can be readily utilized as a basis for the design of other structures, methods, and systems for carrying out the several purposes of the embodiments and claims presented in this application. It is important, therefore, that the claims be regarded as including such equivalent constructions.

What is claimed is:

1. A method for multiplexed analysis comprising:
    acquiring interrogation data associated with encapsulating microstructures in a population at a structure concentration of at least 100 microstructures/µL;
    identifying from the interrogation data at least two multiplexing parameters of at least a portion of the encapsulating microstructures, wherein one of the at least two multiplexing parameters comprises the shape of the encapsulating microstructures, and another of the at least two multiplexing parameters selected from the group consisting of size and fluorescence of the encapsulating microstructures; and
    indexing at least a portion of the encapsulating microstructures based on a pre-determined barcoding system;
    wherein at least one encapsulating microstructure has a different shape than another encapsulating microstructure in the population; and
    wherein at least a portion of the encapsulating microstructures each comprise a hydrogel with suspensions selected from the group consisting of one or more cells, one or more analyte sensing capture agents, and combinations thereof.

2. The method of claim 1, wherein acquiring the interrogation data comprises flowing the population through a flow cytometer.

3. The method of claim 1, wherein acquiring the interrogation data comprises flowing the population through an imaging flow cytometer; and
    wherein the structure concentration is at least $5 \times 10^3$ microstructures/µL.

4. The method of claim 1, wherein the structure concentration is at least $5 \times 10^4$ microstructures/µL.

5. The method of claim 1, wherein the pre-determined barcoding system comprises at least 300 distinct barcodes corresponding to one or more of the multiplexing parameters.

6. The method of claim 1, wherein at least a portion of the encapsulating microstructures each comprise a hydrogel with a suspension of one or more cells selected from group consisting of cancer cells, stem cells, and stromal cells.

7. The method of claim 1, wherein the population comprises at least 3,500 microstructures.

8. The method of claim 1, wherein the population comprises at least 49,500 microstructures.

9. A method for multiplexed analysis comprising:
    non-destructively acquiring interrogation data associated with a population at a structure concentration of at least 100 microstructures/µL, the population comprising microstructures, each microstructure comprising:
    a three-dimensional microgel niche; and
    one or more multiplexing parameters of the microstructures selected from the group consisting of shape, size and fluorescence;
    identifying from the interrogation data at least two multiplexing parameters of at least a portion of the microstructures, one comprising the shape of the microstructures, and another of the at least two multiplexing parameters selected from the group consisting of size and fluorescence of the microstructures;
    indexing at least a portion of the microstructures based on a pre-determined barcoding system comprising barcodes, each barcode different from one another, and each barcode based at least in part on at least one of the multiplexing parameters selected from the group consisting of size and fluorescence of the microstructures; and
    sorting at least a portion of the of the microstructure population based on the indexing;
    wherein at least one microstructure has a different shape than at least another microstructure.

10. The method of claim 9, wherein the structure concentration is at least $5 \times 10^3$ microstructures/µL.

11. The method of claim 9, wherein the microstructure further comprises one or more cells.

12. The method of claim 11, wherein one or more of the cells are selected from group consisting of cancer cells, stem cells, and stromal cells.

13. The method of claim 9, wherein the microstructure further comprises one or more analyte sensing capture agents.

14. The method of claim 9, wherein the pre-determined barcoding system comprises at least 300 distinct barcodes.

15. The method of claim 9, wherein non-destructively acquiring the interrogation data comprises flowing the population through an imaging flow cytometer.

16. The method of claim 9, wherein non-destructively acquiring the interrogation data comprises flowing the population through a flow cytometer.

17. The method of claim 9, wherein the structure concentration is at least $5 \times 10^4$ microstructures/µL.

18. The method of claim 9, wherein the population comprises at least 3,500 microstructures.

19. The method of claim 9, wherein the population comprises at least 49,500 microstructures.

* * * * *